(12) United States Patent
Butzine et al.

(10) Patent No.: US 8,174,358 B2
(45) Date of Patent: May 8, 2012

(54) HANDHELD X-RAY SYSTEM INTERFACE WITH TRACKING FEATURE

(75) Inventors: Jonathan Mark Butzine, Oconomowoc, WI (US); Jeremy Patrick Hannon, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 47 days.

(21) Appl. No.: 12/786,363

(22) Filed: May 24, 2010

(65) Prior Publication Data

US 2011/0291800 A1 Dec. 1, 2011

(51) Int. Cl.
*G08B 5/22* (2006.01)
*G08B 25/00* (2006.01)

(52) U.S. Cl. .......... 340/8.1; 340/12.22; 340/12.33; 340/12.24; 340/12.29; 340/4.1

(58) Field of Classification Search .......... 340/8.1, 340/12.22, 12.23, 12.24, 12.29, 4.1; 378/114, 378/205, 98, 101, 117; 250/338.1, 342; 192/129, 192/130

See application file for complete search history.

(56) References Cited

U.S. PATENT DOCUMENTS

| | | | |
|---|---|---|---|
| 5,206,894 A | | 4/1993 | Makrinos et al. |
| 5,223,875 A | * | 6/1993 | Yanagisawa ............ 396/58 |
| 5,416,819 A | * | 5/1995 | Uzuyama et al. ........ 378/116 |
| 5,526,245 A | * | 6/1996 | Davis et al. ............ 362/233 |
| 5,555,120 A | | 9/1996 | Telymonde et al. |
| 5,675,227 A | | 10/1997 | Roos et al. |
| 5,867,561 A | | 2/1999 | Strasser et al. |
| 6,239,874 B1 | * | 5/2001 | Harwood ............ 356/614 |
| 6,252,358 B1 | | 6/2001 | Xydis et al. |
| 6,285,742 B1 | * | 9/2001 | Haumann et al. ........ 378/116 |
| 6,563,430 B1 | * | 5/2003 | Kemink et al. ......... 340/8.1 |
| 6,608,884 B1 | * | 8/2003 | Mazess et al. ......... 378/98 |
| 6,750,463 B1 | | 6/2004 | Riley |
| 7,023,959 B2 | | 4/2006 | Nakagawa et al. |
| 7,263,166 B2 | | 8/2007 | Sung et al. |
| 7,283,615 B2 | | 10/2007 | Morehead |
| 7,483,516 B2 | | 1/2009 | Coombs |

(Continued)

FOREIGN PATENT DOCUMENTS

CN 200950208 9/2007

(Continued)

OTHER PUBLICATIONS

U.S. Appl. No. 12/786,323, filed May 24, 2010, Jonathan Mark Butzine.

(Continued)

*Primary Examiner* — Nam V Nguyen
(74) *Attorney, Agent, or Firm* — Fletcher Yoder, PC

(57) ABSTRACT

In one embodiment, an X-ray system includes a handheld X-ray interface device. The handheld X-ray interface device includes a wireless interface for communicating with an imaging system and a tracking device configured to provide a location and/or to track movement of the handheld X-ray interface device relative to the imaging system, wherein the location or tracked movement of the handheld X-ray interface device is communicated to the imaging system as an input for at least one control function of the imaging system.

16 Claims, 16 Drawing Sheets

U.S. PATENT DOCUMENTS

| | | | |
|---|---|---|---|
| 7,502,444 B2 * | 3/2009 | Marar | 378/98 |
| 7,890,235 B2 * | 2/2011 | Self et al. | 701/50 |
| 2002/0085681 A1 | 7/2002 | Jensen | |
| 2005/0202843 A1 | 9/2005 | Fors et al. | |
| 2008/0161672 A1 | 7/2008 | Marar | |
| 2008/0240343 A1 | 10/2008 | Jabri et al. | |
| 2010/0104066 A1 | 4/2010 | Foos et al. | |

FOREIGN PATENT DOCUMENTS

| | | |
|---|---|---|
| EP | 1000582 | 7/2005 |
| JP | 2005013310 | 1/2005 |

OTHER PUBLICATIONS

U.S. Appl. No. 12/786,332, filed May 24, 2010, Jonathan Mark Butzine.

U.S. Appl. No. 12/786,357, filed May 24, 2010, Jonathan Mark Butzine.

EP Search Report from corresponding EP Application No. 11166707.7, Aug. 8, 2011.

* cited by examiner

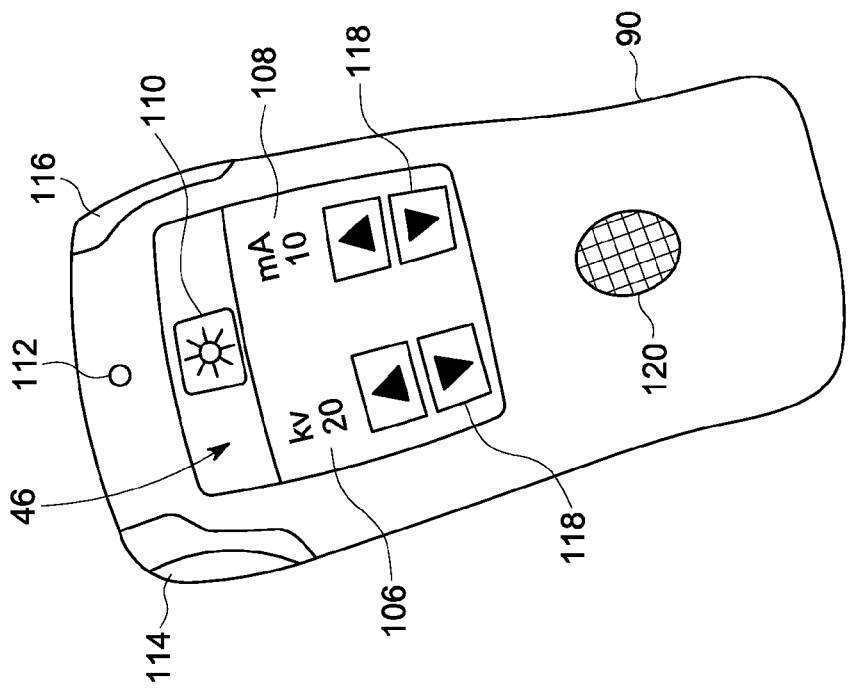
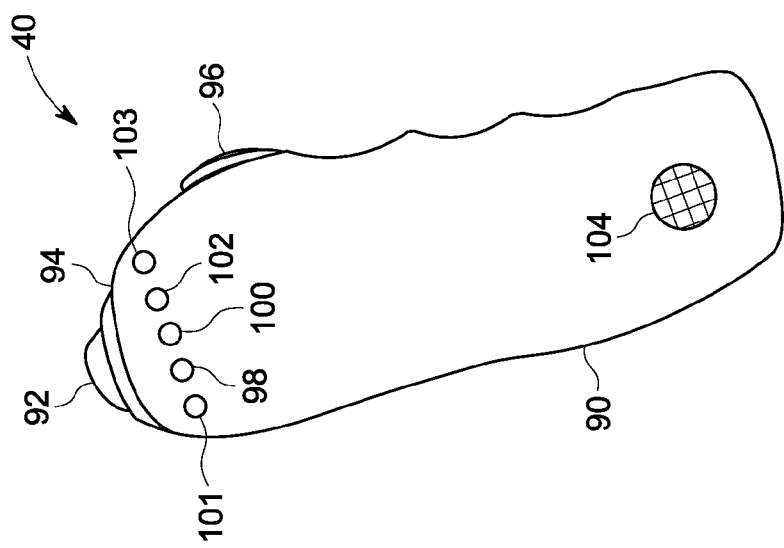
FIG. 5
FIG. 4

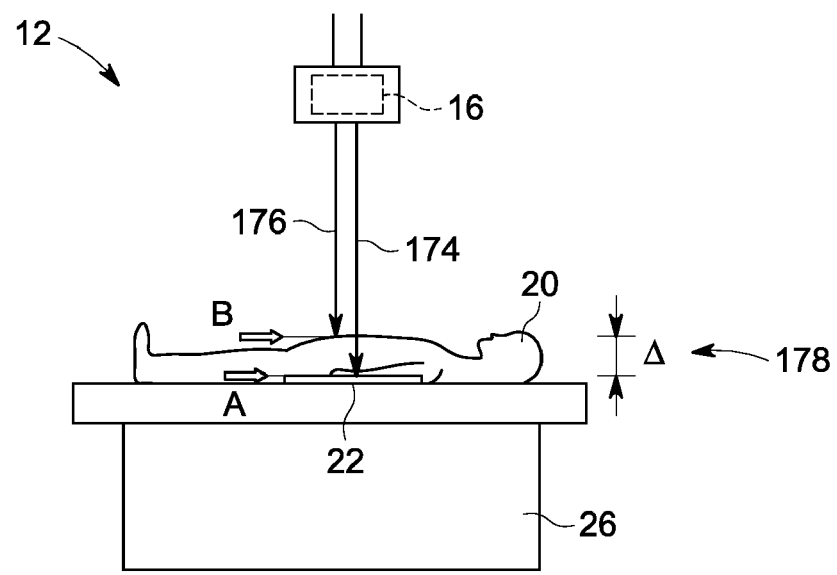
FIG. 14
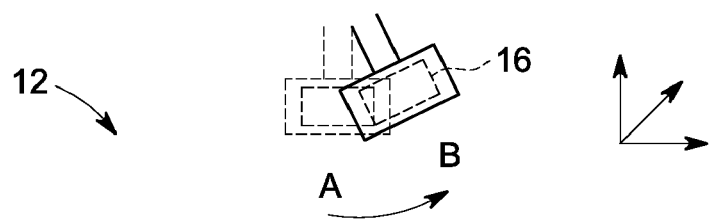
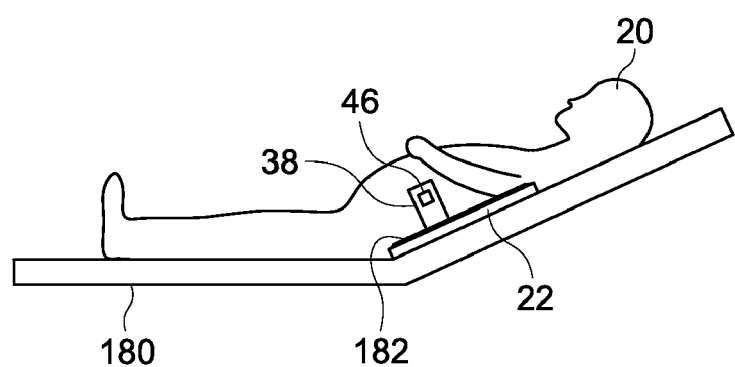
FIG. 15

HANDHELD X-RAY SYSTEM INTERFACE WITH TRACKING FEATURE

BACKGROUND OF THE INVENTION

The subject matter disclosed herein relates to X-ray imaging systems and more particularly to X-ray imaging systems that use a handheld interface device.

X-ray systems are widely employed in medical environments, such as hospitals. Typically, where possible the X-ray technician is positioned away from the location of exposure, and often behind a shielded barrier to avoid or reduce exposure to radiation. Often the X-ray systems include an exposure switch, or handswitch, attached to a cord, which is in signal communication with a control console of the X-ray system and that allows the technician to make the exposure from a distance (e.g., by pressing a button on the handswitch), sometimes outside of the examination room.

Often patients undergoing X-ray examinations are positioned in difficult or awkward positions for a variety of reasons. The technician must adjust the X-ray system accordingly. However, when the technician is not physically in close proximity to the X-ray system it may be difficult for the technician to interact with the X-ray system. In addition, the technician must return to the console between every exposure to analyze the imaging data and to determine if the patient was properly positioned or if the X-ray source was properly aligned with a detector. The technician may have to expose the patient to needless exposures in trying to obtain the optimal image. Thus, the need for a handswitch arrangement to overcome these difficulties.

BRIEF DESCRIPTION OF THE INVENTION

In accordance with one embodiment, an X-ray system includes an imaging system. The imaging system includes a source of X-ray radiation, an X-ray image receptor, control circuitry for controlling the source of X-ray radiation, and a wireless interface. The X-ray system also includes a handheld interface device configured to communicate wirelessly with the imaging system. The imaging system is configured to track a location of the handheld interface device and to use the location as an input for at least one control function of the imaging system.

In accordance with another embodiment, an X-ray system includes a handheld X-ray interface device. The handheld X-ray interface device includes a wireless interface for communicating with an imaging system and a tracking device configured to provide a location and/or to track movement of the handheld X-ray interface device relative to the imaging system, wherein the location or tracked movement of the handheld X-ray interface device is communicated to the imaging system as an input for at least one control function of imaging system.

In accordance with a further embodiment, a method for tracking the location of a handheld interface device includes establishing wireless communication between an imaging system and a handheld interface device, the imaging system includes a source of X-ray radiation, an X-ray detector, control circuitry for controlling the source of X-ray radiation, and a first wireless interface, the handheld interface device includes a second wireless interface for communicating wirelessly with the imaging system and a tracking device configured to provide a location and to track movement of the handheld interface device. The method also includes transmitting the location or tracked movement of the handheld interface device relative to the imaging system.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein:

FIG. 4 is a perspective view of a handheld interface device in FIGS. 1 and 2;

FIG. 5 is a perspective view of another handheld interface device in FIGS. 1 and 2;

FIG. 14 is a perspective view of determining various exposure parameters using the handheld interface device, in accordance with aspects of the present technique;

FIG. 15 is a perspective view of determining orthogonality between the X-ray source and the image receptor, in accordance with aspects of the present technique;

DETAILED DESCRIPTION OF THE INVENTION

Figure 1:
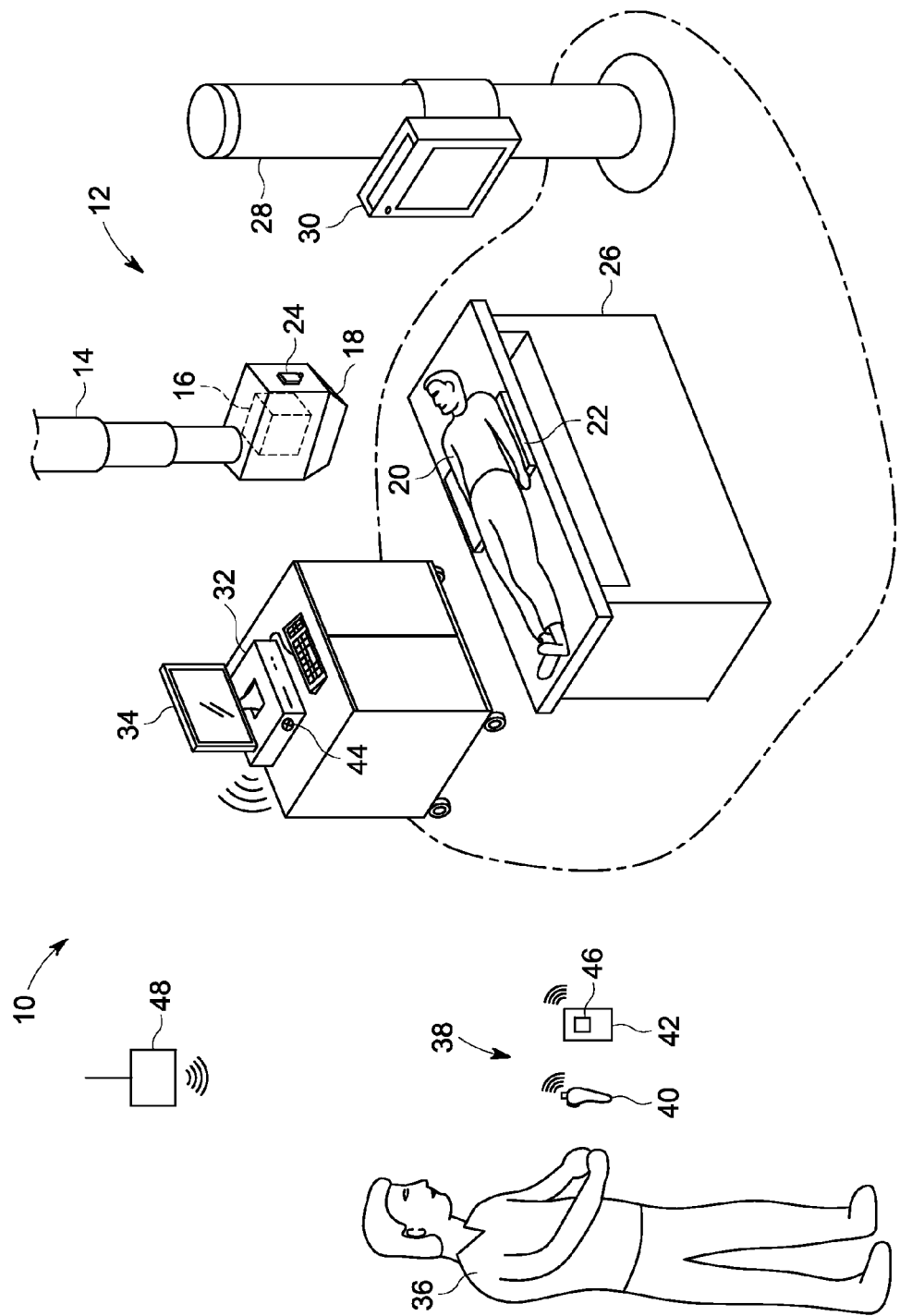
FIG. 1 is a perspective view of a fixed X-ray system, equipped in accordance with aspects of the present technique.

Referring generally to FIG. 1, an X-ray system is represented, referenced generally by reference numeral 10. In the illustrated embodiment, the X-ray system 10 may be a digital or analog X-ray system. The X-ray system 10 is designed both to acquire original images or image data and to process the image data for display (in a digital X-ray system) in accordance with the present technique.

In the embodiment illustrated in FIG. 1, the X-ray system 10 includes an imaging system 12. The imaging system 12 includes an overhead tube support arm 14 for positioning a radiation source 16, such as an X-ray tube, and a collimator 18 with respect to a patient 20 and an image receptor 22. In analog X-ray systems 10, the image receptor 22 may include a radiographic film and cassette, phosphorescent screen and computed radiography cassette, or other device. In digital X-ray systems, the image receptor 22 may include a digital X-ray detector. The imaging system 12 may also include a camera 24 to help facilitate the positioning of the radiation source 16 and collimator 18. Moreover, in one embodiment, the imaging system 12 may be used in consort with one or both of a patient table 26 and a wall stand 28 to facilitate image acquisition. Particularly, the table 26 and the wall stand 28 may be configured to receive image receptor 22. For instance, image receptor 22 may be placed on an upper, lower or intermediate surface of the table 26, and the patient 20 (more specifically, an anatomy of interest of the patient 20) may be positioned on the table 26 between the image receptor 22 and the radiation source 16. Also, the wall stand 28 may include a receiving structure 30 also adapted to receive the image receptor 22, and the patient 20 may be positioned adjacent the wall stand 28 to enable the image or image data to be acquired via the image receptor 22. The receiving structure 30 may be moved vertically along the wall stand 28.

Also depicted in FIG. 1, the imaging system 12 includes a workstation 32 and display 34. In one embodiment, the workstation 32 may include or provide the functionality of the imaging system 12 such that a user 36, by interacting with the workstation 32 may control operation of the source 16 and detector 22 (in a digital X-ray system 10). In other embodiments, the functions of the imaging system 12 may be decentralized, such that some functions of the imaging system 12 are performed at the workstation 32, while other functions are performed by another component of the X-ray system 10, such as a handheld interface device 38. The handheld interface device 38 is configured to be held by a user 36 and to communicate wirelessly with the imaging system 12. The handheld interface device 38 is also configured to prepare the imaging system 12 for an exposure and to initiate an exposure. The imaging system 12 is configured to wirelessly communicate system operational data to the handheld interface device 38 and the handheld interface device 38 is configured to provide a user detectable indication of the operational status based on the data. In one embodiment, the handheld interface device 38 (e.g., 40) is simply designed to prepare and initiate an exposure, as well as to receive system operational data and to provide an indication of the data. It is noted that the imaging system 12 and handheld interface device 38 may utilize any suitable wireless communication protocol, such as an IEEE 802.15.4 protocol, an ultra wideband (UWB) communication standard, a Bluetooth communication standard, or any IEEE 802.11 communication standard.

In another embodiment, the handheld interface device 38 (e.g., 42) is configured to receive a user-input command for operation of the imaging system 12 (e.g., changing X-ray source settings or moving the receiving structure 30 along the wall stand 28) prior to initiation of an X-ray exposure sequence and to wirelessly transmit the command to the imaging system 12. For example, the imaging system 12 may include a speaker 44 to transmit patient-audible commands to the patient 20 in response to a signal from the handheld interface device 42. The speaker 44 may be located on the operator workstation 34, near the radiation source 16, in the table 26, or another location. In response to wirelessly receiving the command from the handheld interface device 42 the imaging system 12 executes the command. Also, the handheld interface device 42 includes a user-viewable screen 46 and is configured to receive and display patient data on the screen 46. The imaging system 12 is configured to communicate patient data or instructions to the handheld interface device 42. In one embodiment, the workstation 32 may be configured to function as a server of instructions and/or content on a network 48 of the medical facility, such as a hospital information system (HIS), a radiology information system (RIS), and/or picture archiving communication system (PACS), and to provide these instructions and/or content to the handheld interface device 42. Alternatively, the network 48 may wirelessly communicate directly with the handheld interface device 42.

Further, the handheld interface device 42 may be configured to be tracked by the imaging system 12. The imaging system 12 is configured to track the location and/or movement of the handheld interface device 42 and to use the location and/or movement as input to control at least one function of the system 12 (e.g., movement of the X-ray source 16).

In one embodiment, the imaging system 12 may be a stationary system disposed in a fixed X-ray imaging room, such as that generally depicted in and described above with respect to FIG. 1. It will be appreciated, however, that the presently disclosed techniques may also be employed with other imaging systems, including mobile X-ray units and systems, in other embodiments.

Figure 2:
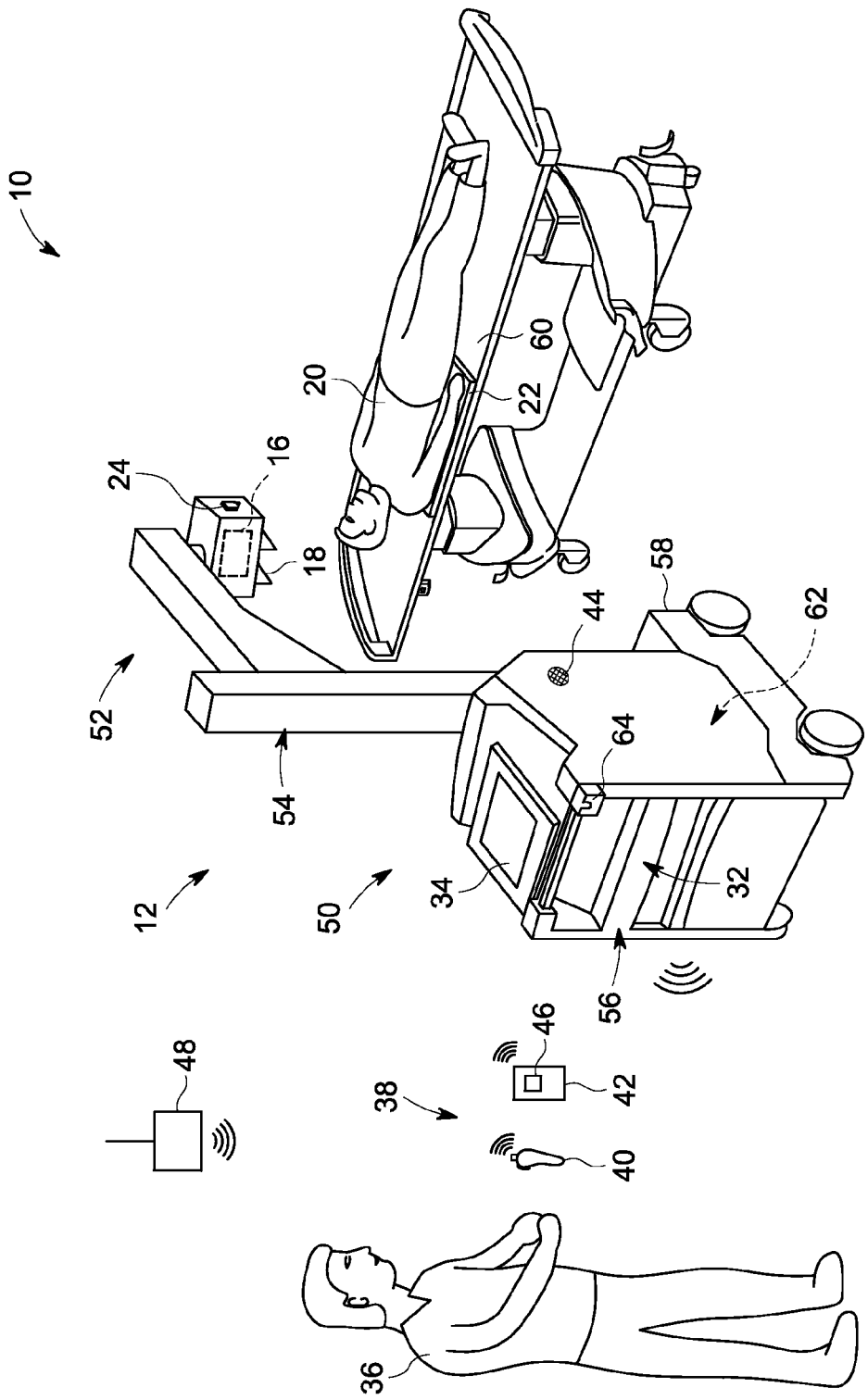
FIG. 2 is a perspective view of a mobile X-ray system, equipped in accordance with aspects of the present technique.

For instance, as illustrated in the X-ray system of FIG. 2, the imaging system 12 may be moved to a patient recovery room, an emergency room, a surgical room, or any other space to enable imaging of the patient 20 without requiring transport of the patient 20 to a dedicated (i.e., fixed) X-ray imaging room. The imaging system 12 includes a mobile X-ray base station 50 and image receptor 22. As mentioned above, the X-ray system 10 may be digital or analog. In one embodiment, a support arm 52 may be vertically moved along a support column 54 to facilitate positioning of the radiation source 16 and collimator 18 with respect to the patient 20. Further, one or both of the support arm 52 and support column 54 may also be configured to allow rotation of the radiation source 16 about an axis. The X-ray base station 50 may also include camera 24 to assist in positioning of the radiation source 16 and collimator 18, as well as speaker 44 to transmit patient-audible commands as described above. In addition, the X-ray base station 50 includes a speaker located either on a base unit 56, the column 54, or the arm 52, or another location of the X-ray base station 50. Further, the X-ray base station 50 has a wheeled base 58 for movement of the station 50.

The patient 20 may be located on a bed 60 (or gurney, table or any other support) between the X-ray source 24 and the image receptor 22 and subjected to X-rays that pass through the patient 20 and are received by either a film, phosphorescent screen, or other medium. During an imaging sequence using the digital X-ray system 10, the detector 22 receives X-rays that pass through the patient 20 and transmits imaging data to a base unit 56. The detector 22 is in communication with the base unit 56. The base unit 56 houses systems electronic circuitry 62 that acquires image data from the detector 22 and that, where properly equipped, may process the data to form desired images. In addition, the systems electronic circuitry 62 both provides and controls power to the X-ray source 16 and the wheeled base 58 in either the digital or analog X-ray system 10. The base unit 56 also has the operator workstation 32 and display 34 that enables the user 36 to operate the X-ray system 10. The operator workstation 32 may include buttons, switches, or the like to facilitate operation of the X-ray source 16 and detector 22.

Similar to the X-ray system 10 in FIG. 1, functions of the imaging system 12 may be performed by the handheld interface device 38. As described above, the imaging system 12 and the handheld interface device 38 are configured to communicate wirelessly with each other. In addition, the handheld interface device 38 can be configured to communicate wirelessly with the medical facility network 48, as described above. As above, the user 36 may utilize the handheld interface device 40 designed to prepare and initiate an exposure, as well as to receive system operational data and to provide an indication of the data. Alternatively, the user 36 may utilize the handheld interface device 42, described above, to input user commands for operation of the imaging system 12 (e.g., the movement of the X-ray base station 50). In addition, the handheld interface device 42 includes screen 46 for the display of patient data, image data (in digital systems 10), instructions, as well as other information. Further, the handheld interface device 42 may be configured to be tracked, as described above. Tracking of the handheld interface device 42 may provide input to the X-ray base station 50 to follow the handheld interface device 42 as described below. The X-ray base station 50 has a holder or cradle 64 for the handheld interface device 38 when the device 38 is not in use. The cradle 64 may be configured to recharge the battery of the handheld interface 38, either through conductive charge contacts or with a contactless method such as inductive or capacitive charging.

Figure 3:
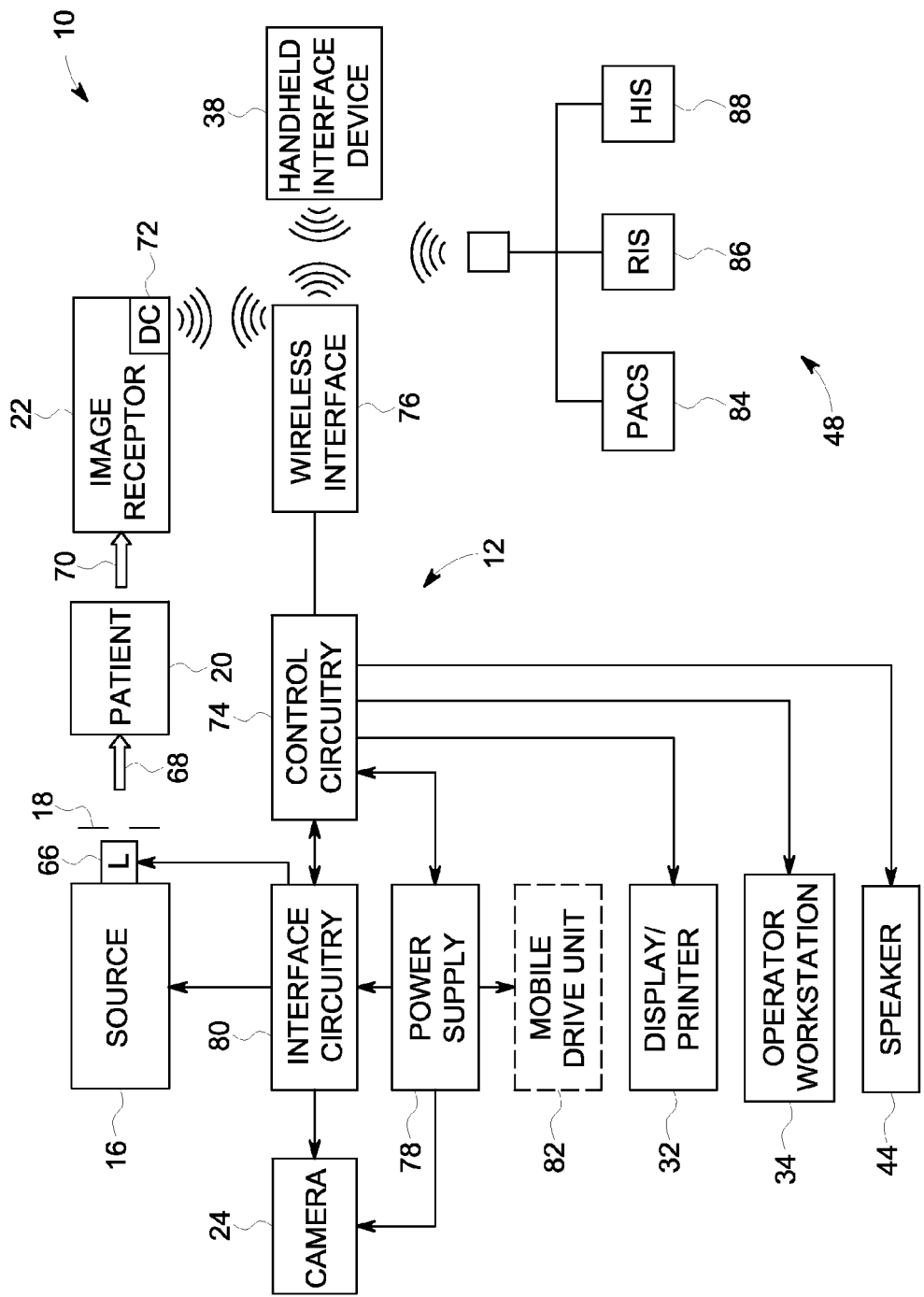
FIG. 3 is a diagrammatical overview of the X-ray systems in FIGS. 1 and 2.

FIG. 3 illustrates diagrammatically the X-ray systems 10 described in FIGS. 1 and 2, in particular, digital X-ray systems 10, although some of the below description applies to analog X-ray systems 10 as well. As illustrated in FIG. 3, the X-ray system 10 includes the source of X-ray radiation 16 positioned adjacent to the collimator 18. A light source 66, also known as a collimator light, is positioned between the X-ray source 16 and the collimator 18. The collimator 18 permits a stream of radiation 68 or light to be directed to a specific region in which an object or subject, such as the patient 20, is positioned. A portion 70 of the radiation passes through or around the subject and impacts the image receptor or digital X-ray detector 22. As will be appreciated by those skilled in the art, the detector 22 in digital X-ray systems 10 converts the X-ray photons received on its surface to lower energy photons, and subsequently to electric signals, which are acquired and processed to reconstruct an image of the features within the subject. The collimator light 66 in the collimator 18 directs light onto the same area where the X-ray photons will pass and can be used to position the patient 20 before exposure. The collimator light 66 can be turned on and off with a user input on the imaging system 12 or on the handheld interface device 38.

Moreover in digital X-ray systems, the detector 22 is coupled to a detector controller 72 which commands acquisition of the signals generated in the detector 22. The detector controller 26 may also execute various signal processing and filtration functions, such as for initial adjustment of dynamic ranges, interleaving of digital image data, and so forth. The detector controller 26 is responsive to signals from control circuitry 74 communicated wirelessly via a wireless interface 76. In general, the control circuitry 74 commands operation of the imaging system 12 to execute examination protocols and to process acquired image data (in digital X-ray systems 10). In the present context, the control circuitry 74 also includes signal processing circuitry, typically based upon a programmed general purpose or application-specific digital computer; and associated devices, such as optical memory devices, magnetic memory devices, or solid-state memory devices, for storing programs and routines executed by a processor of the computer to carry out various functionalities, as well as for storing configuration parameters and image data; interface circuits; and so forth.

In both digital and analog X-ray systems 10, the radiation source 16 is controlled by the control circuitry 74 which controls signals for examination sequences. For example, the control circuitry 74 can inhibit the operation of the radiation source 16 if the correct examination conditions are not in place. In addition, the control circuitry 74 controls a power supply 78 which supplies power to the radiation source 16, light source 66, camera 24, as well the control circuitry 74. Interface circuitry 80 facilitates the provision of power to the radiation source 16, light source 66, camera 24, and control circuitry 74. The power supply 78 also provides power to a mobile drive unit 82 (in mobile X-ray systems) to drive the movement of the wheeled base 58 of the X-ray base station 50.

In the embodiment illustrated in FIG. 1, the control circuitry 74 is linked to at least one output device, such as the display or printer 34. The output device may include standard or special purpose computer monitors and associated processing circuitry. One or more operator workstations 34 may be further linked in the system for outputting system parameters, requesting examinations, viewing images (in digital X-ray systems 10), and so forth. In general, displays, printers, workstations, and similar devices supplied within the system may be local to the imaging components, or may be remote from these components, such as elsewhere within an institution or hospital, or in an entirely different location, linked to the imaging system 12 via one or more configurable networks, such as the Internet, virtual private networks, and so forth. The control circuitry 74 may also be linked to the speaker 44 which provides audible signals such as locator signals or patient-audible commands.

Via the wireless interface 76 the imaging system 12 communicates wirelessly with the handheld interface device 38. The control circuitry 74 provides the handheld interface device 38 system operational data (e.g., inhibit of operation of radiation source), images reconstructed from image data from the detector 22 (in digital X-ray systems 10), images of the patient 20 generated by the camera 24, and patient data, as well as other information. The handheld interface device 38 wirelessly communicates a signal to prepare for and initiate an exposure and other commands for operation of the imaging system 12, as well the location and/or movement of the device 38 relative to the system 12. Besides receiving patient data and/or instructions from the imaging system 12, the handheld interface device 38 wirelessly receives patient information and/or instructions (e.g., imaging sequences to be performed) from the medical facility's network 48. The medical facility network 48 includes PACS 84, RIS 86, and/or HIS 88 to provide the information and/or instructions. The network 48 may also communicate the patient information and/or instructions to imaging system 12, which may then provide the information and/or instructions to the handheld interface device 38.

As mentioned above, the handheld interface device 38 may include a simple embodiment of the device 40 to prepare for and initiate an exposure, as well as to receive system operational data and to provide an indication of the data. In addition, the handheld interface device 40 is configured to provide user detectable indications of the operational status of the imaging system 12. FIG. 4 illustrates the handheld interface device 40 of FIGS. 1 and 2. The handheld interface device 40 includes an exterior housing 90 that is suitably dimensioned to fit in the hand of the user. The handheld interface device 40 can be configured to be paired with a single X-ray system 10. The handheld interface device 40 is configured to provide user detectable indications of the operational status of the imaging system 12. The handheld interface device 40 includes a prepare/exposure push button 92 located at the top 94 of the device 40. The prepare/exposure button 92 may operate in a variety of ways. In one embodiment, pressing the button 92 a first time may prepare the X-ray system 10 for an exposure (i.e., the rotor encasing the radiation source 16 begins spinning). Pressing the button 92 a second time may initiate the exposure by the X-ray system 10. The button 92 may be inhibited from being pressed the second time if the X-ray system 10 has not finished preparations for the exposure. Alternatively, the button 92 may be partially pressed to a first position to prepare the X-ray system 10 for the exposure and further pressed to a second position to initiate the exposure. The button 92 may be inhibited from being pressed to the second position if the X-ray system 10 has not finished preparations for the exposure. In either embodiment, the button 92 is configured to not command the system to initiate an exposure when the operation of X-ray source 16 is inhibited. The handheld interface device 40 also includes a collimator light button 96 disposed on the exterior housing 90. Pressing the collimator light button 96 may command the system to activate or deactivate the collimator light 66. The handheld interface device 40 is configured to go to sleep when not in use. Pressing the prepare/exposure 92 and/or collimator light button 96 may also shift the device 40 from sleep mode to operational mode. In other embodiments, the handheld interface device 40 may include additional buttons for other features.

The handheld interface device 40 may also include one or more light emitting diodes (LEDs) to indicate the operational status of the imaging system 12. For example, the handheld interface device 40 may include a power status (battery status) LED 98 to indicate the power level of the device 40. The power status LED 98 may indicate the power status of the device 40 in a variety of ways. For example, the power status LED 98 may only illuminate when the device 40 has sufficient power. If the device 40 has low power, the LED 98 may blink or not be illuminated. Alternatively, the LED 98 may only illuminate when the power of the handheld interface device 40 is low. In a further alternative, the LED 98 may illuminate a specific color for a specific power status of the device 40, such as green for sufficient power and red for low power. The handheld interface device 40 can also include a charge status LED 100 for the battery or power supply 78 that powers the X-ray source 16 and/or mobile drive unit 82 of the imaging system 12. The LED 100 may be designed to function similarly to the power status LED 98 to indicate the status of the power supply 78. The handheld interface device 40 also includes an X-ray exposure LED 102 to indicate when an exposure by the imaging system 12 is occurring. The LED 102 of the device 40 illuminates during the exposure. An LED 101 could indicate an inhibit on the imaging system 12 that currently prevents exposure initiation. An LED 103 could indicate that wireless communication is occurring. A combination of the LEDs could indicate that the wireless handheld interface device 40 is in the process of or has completed association or pairing with imaging system 12. Alternative embodiments may include additional LEDS to provide an indication of system operation data. The handheld interface device 40 also includes a speaker 104. The speaker 104 can provide an audible tone or tone sequence during the occurrence of the exposure. Also, the speaker 104 may provide an audible tone for a locator signal as described below.

FIG. 5 illustrates the handheld interface device 42 of FIGS. 1 and 2 that includes similar and additional features. The handheld interface device 42 may be based upon or include a personal digital assistant, a multipurpose cellular telephone, or other handheld device. The handheld interface device 42 includes an exterior housing 90 that is suitably dimensioned to fit in the hand of the user. The handheld interface device 42 is configured to be paired with the single X-ray system 10 and to provide user detectable indications of the operational status of the imaging system 12. In addition, the handheld interface device 42 is configured to receive a user-input command for operation of the imaging system 12, as well as patient data and/or instructions. Further, the handheld interface device 42 is configured to have the location and/or movement of the device 42 tracked by the imaging system 12 to be used by the system 12 as an input for one or more control functions of the system 12. The handheld interface device 42 includes screen 46 and a combination of buttons and LEDs to interact with the imaging system 12. The screen 46 is configured display system operational data and X-ray system or exposure settings. For example, the screen 46 may display the exposure parameters such as a kilovolt peak setting 106, a milliamp setting 108, or other settings such as a milliamp-second setting. The screen 46 may include one or more icons 110 that represent system operational data. For example, the icons 110 may represent the charge status of the power supply 78 to the X-ray source 16 and/or mobile drive unit 82, power status of the device 42, readiness of X-ray system 10 for exposure, inhibition of the X-ray source 16, an exposure in progress, a wireless link connection, and other operational data. The screen 46 is also configured to display patient data, instructions, and images. The handheld interface device 42 may also include LEDS to indicate system operational data as described with device 40. For example, LED 112 may illuminate when an exposure is in progress.

Additionally, the handheld interface device 42 may include buttons 114 and 116, which may be actual depressible switches, regions of a touch screen, or any other suitable user interface. The buttons 114 and 116 may be used to input commands for the imaging system 12 to execute. These commands may be used for multiple functions when pressed, including preparing and initiating an exposure by the system 12, operating the collimator light 66, inputting the location of the device 42 with respect to the system 12 (e.g., to calculate a source-to-image distance), and other functions. The buttons 114 and 116 when used as a prepare/expose button may not be pressed when operation of the X-ray source 16 is inhibited.

In addition, the screen 46 of the handheld interface device 42 may include a touch-screen to allow the user to interface with the system 12 and to input commands for the operation of the system 12. The screen 46 may allow the user to select from a variety of modes to operate the imaging system 12. For example, the screen 46 may include exposure parameters 106 and 108, described above, as well as arrows 118 to change the settings of the exposure parameters 106 and 108. Instead of the buttons 114 and 116, the screen 46 may be used to prepare for and initiate the system 12 for an exposure. Further, the handheld interface device 42 includes a speaker/recorder 120. The speaker 120 provides an audible tone during exposures. Also, the speaker 104 may provide an audible tone for a locator signal as described below. Further, the speaker 104 may serve as a microphone, or a separate microphone (not shown) may be provided and the device configured to act as a recorder to allow the user to dictate voice inputs. The voice inputs may then be recorded by the device 42 and/or in the X-ray system 10, the HIS, RIS or PACS and associated with an X-ray imaging sequence.

Figure 6:
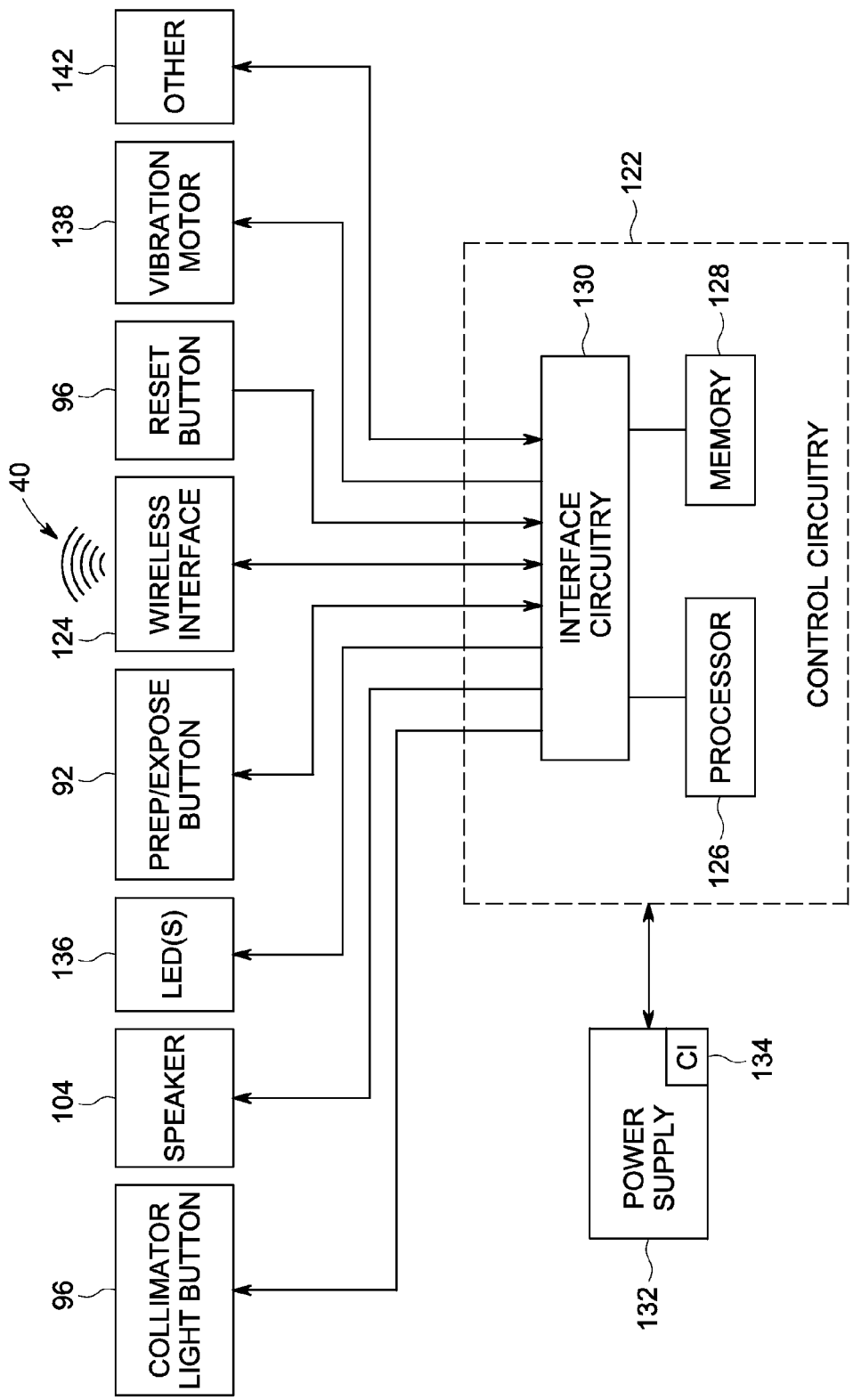
FIG. 6 is a diagrammatical overview of the handheld interface device in FIG. 4.

FIG. 6 illustrates a diagrammatical overview of the handheld interface device 40. The handheld interface device 40 includes a control circuitry 122 to control the various functions of the device 40 and a wireless interface 124 to communicate with the imaging system 12. The wireless interface 124 may utilize any suitable wireless communication protocol, such as an IEEE 802.15.4 protocol, an ultra wideband (UWB) communication standard, a Bluetooth communication standard, or any IEEE 802.11 communication standard. The control circuitry 122 includes a processor 126 to process the various signals received via the wireless interface 124 from the system 12. In addition, the processor 126 receives input signals from input devices and generates command signals to be transmitted to the system 12 via the wireless interface 124. The control circuitry 122 also includes a memory 128 for storing programs and routines executed by the processor 126, as well as configuration parameters of the handheld interface device 40. The processor 126 and memory 128 are connected to interface circuitry 130 that interacts with the input and output devices of the handheld interface device 40 to receive input signals from the input devices and to transmit output signals to the output devices and/or wireless interface 124.

The control circuitry 122 is powered and in communication with a power supply 132. The power supply 132 may be a rechargeable battery (e.g., a thin film battery). The power supply 132 includes a charging interface 134 configured for charging of the power supply 132 when the handheld interface device 40 is located in a charger (e.g., the cradle 64 of the X-ray base station 50). The charge cradle 64 can charge the power supply 132 of the handheld interface device 40 either through conductive charge contacts or through inductive or capacitive contactless charging methods. Alternatively, the power supply 132 may include photovoltaic cells to recharge the handheld interface device 40. Further, the power supply 132 may include a device to harvest radiofrequency energy or piezoelectric energy (e.g., microelectricalmechanical system (MEMS) device).

The interface circuitry 130 receives system operational data from the system 12 via the wireless interface 124 and transmits the data to the processor 126. Once the data is processed a signal is generated by the processor 126 and transmitted via the interface circuitry 130 to the output devices. For example, the handheld interface device 40 may receive a command from imaging system 12 to locate the device 40. The speaker 104 may generate a locator signal in response to the command. The speaker 104 may also generate a user audible tone when an exposure is taking place. The speaker 104 may generate an audible tone if the handheld device 40 is out of the charge cradle 64 for a minimum time. Also, various LEDS 136 may be illuminated to provide the user an indication of the system operational status as described above. Further, besides a visual and audible indication of an exposure, the handheld interface device 40 includes a vibrating motor 138 to vibrate and provide a tactile indication of the occurrence of an exposure in progress.

The handheld interface device 40 also provides commands to the imaging system 12. For example, as described above, the device 40 may include a collimator light button 96 to activate and deactivate the collimator light 66, and the prepare/expose button 92 to prepare and initiate exposures with the system 12. Input signals received from these buttons 140, 92, and 96 generate command signals wirelessly transmitted to the system 12 for execution. The handheld interface device 40 may include other devices 142 besides the input and output devices described for operation of the device 40. For example, other devices 142 may include a tracking device, as described below, or a flash light.

Figure 7:
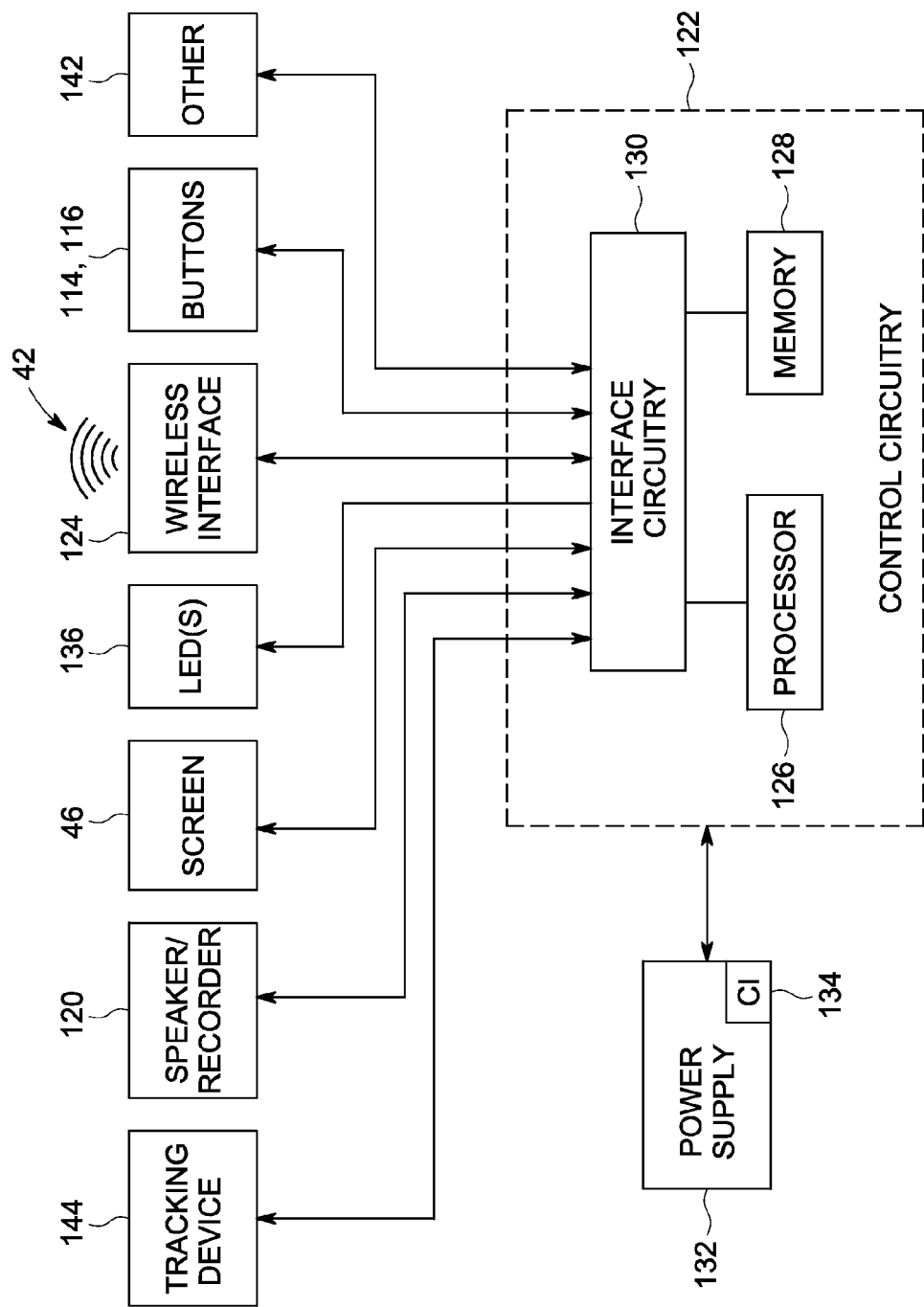
FIG. 7 is a diagrammatical overview of the handheld interface device in FIG. 5.

FIG. 7 illustrates a diagrammatical overview of the handheld interface device 42. The handheld interface device 42 includes control circuitry 122, power supply 132, and wireless interface 124 similar to the embodiment in FIG. 6. However, the memory 128 is also capable of storing images transmitted from the imaging system 12 (in digital X-ray systems 10), patient data/and or instructions received from the system 12 or network 48, system operational data (e.g., dose area product to be embedded in image sequences), and user input (e.g., audible recordings to be associated with an imaging sequence). As described above, the handheld interface device 42 includes one or more LEDS 136 to provide user detectable indications of the system operational data of the imaging system 12.

The handheld interface device 42 also includes the screen 46 to display system operational data, such as in the form of icons 110 as shown in FIG. 5. The system operational data may also be displayed in other forms on the screen 46 (e.g., textual or numerical form). For example, exposure parameter settings 106 and 108 may be presented on the screen 46. The screen 46 may also include a touch-screen 46 capable of encoding inputs by touch. For example, a gesture on the touch-screen 46 (e.g., pressing an arrow displayed on the touch-screen 46 in FIG. 5) may be user input. In some embodiments, the gesture may be interpreted as a multi-point gesture. Images of the patient 20 received via the camera 24 or network 48 may also be displayed on the screen 46. Alternatively, a still image of the patient 20 or a generic image of an anatomical region of the patient 20 may also be displayed on the screen 46. The user may be able to input a location on the anatomy of the patient 20 to be imaged by touching the portion of the anatomy on the touch-screen 46, as described below.

Also, as described above, the device 42 may include a speaker/recorder 120. The speaker 120 allows for the output of an audible tone or tone sequence during an exposure. In addition, the speaker 120 may output a locator signal in response to a command from the imaging system 12 to locate the device 42. The speaker 120 also allows the recording of user-dictated voice inputs that may be recorded and stored in the memory 128 for association with an X-ray image sequence. Also, the user-dictated voice input may be transmitted via the wireless interface 124 to the imaging system 12 to be emitted for the hearing of the patient 20 undergoing X-ray imaging.

As mentioned above, the handheld interface device 42 may include buttons 114 and 116 to allow the user to make various inputs. For example, the buttons 114 and 116 may be used to prepare and initiate an exposure or operate the collimator light 66. Alternatively, these functions, as well as others, may be carried out using inputs via the touch-screen 46. The buttons 114 and 116 may be used in conjunction with other devices of the handheld interface device 142. For example, the device may include a tracking device 144. The tracking device 144 may comprise various inertial measurement units such as an accelerometer, a magnetometer, an inclinometer, and/or a gyroscope. These inertial measurement units allow the relative position and rotation of the device 42 to be tracked in a 3-D coordinate system. The imaging system 12 is configured to track the location and/or movement of the device 42 as received from the tracking device 144 via the wireless interface 124. The location and/or movement of the device 42 are used as input to control functions of the system 12. The tracking device 144 may be used with another input device (e.g., the buttons 114 and 116 or touch-screen 46) to record one or more locations of the device 42 to allow the system 12 to calculate various system operational parameters or to setup the desired imaging sequence. Further, the tracking device 144 may be used by the imaging system 12 to monitor the presence of the handheld interface device 42 within the operative range of system 12. If the handheld interface device 42 is moved outside the operative range of the system 12, the system 12 may send a command to the device 42 to generate an audible tone via the speaker 120.

Similar to device 40, the handheld interface device 42 may include other devices 142 besides the input and output devices described above for operation of the device 42. All of these devices may be used separately or in combination to receive input commands for the operation of the imaging system 12 and to transmit these commands to the system 12 for execution.

Figure 8:
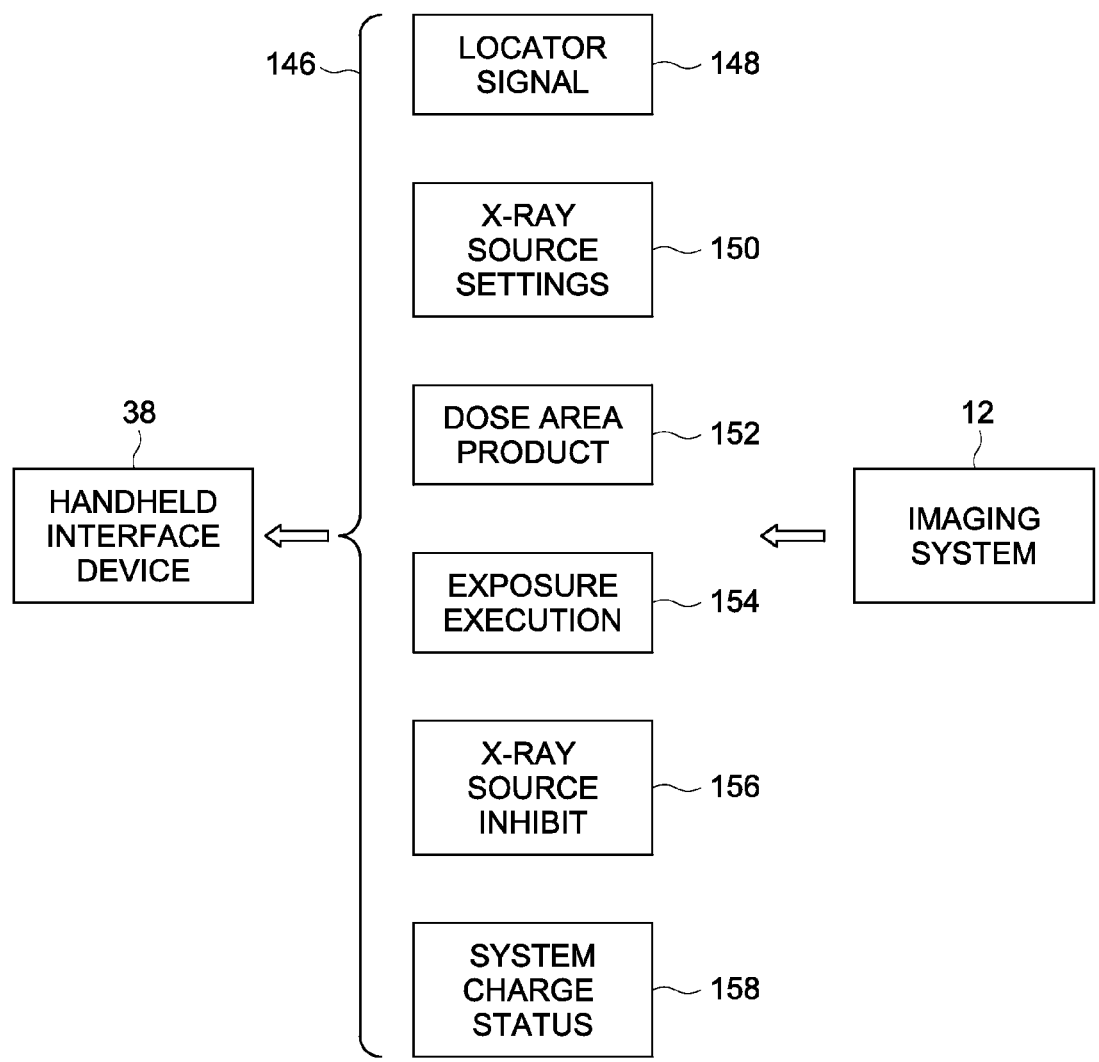
FIG. 8 is a diagrammatical overview of system operational data received by handheld interface devices, in accordance with aspects of the present technique.

As mentioned above, the handheld interface device 38 is configured to receive system operational data wirelessly communicated from the imaging system 12 and to provide a user detectable indication of the imaging system operational status based on the data. FIG. 8 illustrates an exemplary type of system operational data 146 received by the handheld interface device 38 by the imaging system 12. The types of system operational data 146 illustrated are only examples and other types of system operational data 146 may be presented. The system operational data 146 includes a locator signal 148 when the handheld interface device 38 cannot be found by the user. Other system operational data 146 includes X-ray source settings 150. These may include a kilovolt peak setting, a milliamp setting, and a milliamp-second setting. The system operational data 146 includes a dose area product 152. The dose area product 152 reflects the dosage of radiation, as well as the volume of tissue irradiated, with each image sequence. Also, an execution of a current exposure 154 is included. The system 12 ceases transmitting this particular system operational data 146 when the exposure execution 154 concludes. When operation of the X-ray source 16 is inhibited, the device 38 receives an X-ray source inhibit 156, as described above. Further, the system operational data 146 includes a system charge status 158 for the power supply 78 of the imaging system 12 that powers the X-ray source 16 and the mobile drive unit 82 (in mobile systems).

Figure 9:
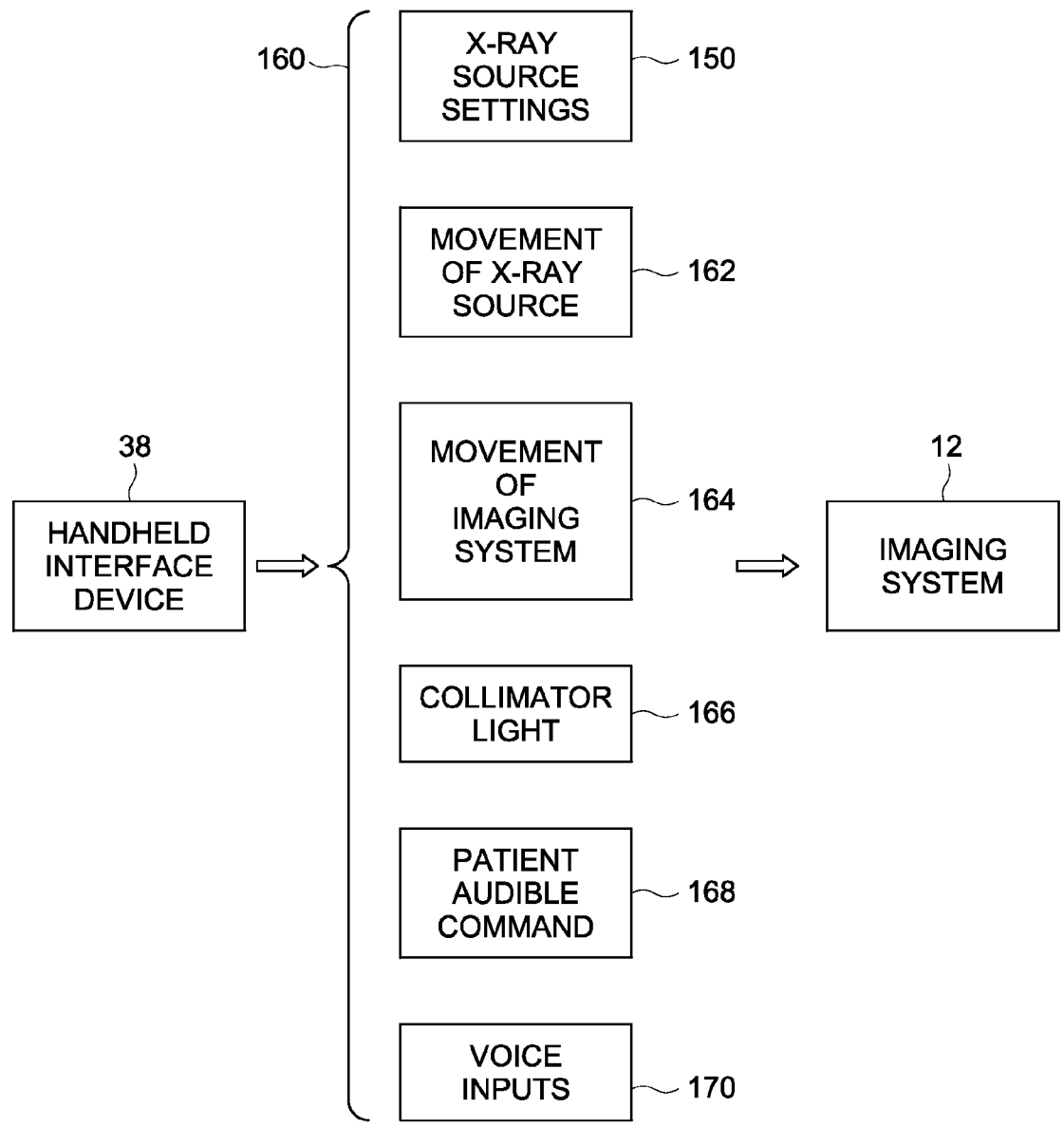
FIG. 9 is a diagrammatical overview of user-input and user-input commands received and transmitted by handheld interface devices, in accordance with aspects of the present technique.

Besides receiving system operational data 146, the handheld interface device 38 may also be configured to receive user-input commands for operation of the imaging system 12. FIG. 9 illustrates various user-input and/or user-input commands 160 received by the handheld interface device 38 and wirelessly transmitted to the imaging system 12. As previously mentioned, the user-input commands 160 include X-ray source settings 150. The command for X-ray source settings 150 may include settings for exposure parameters of the X-ray source 16, such as the kilovolt peak setting, the milliamp setting, the milliamp-second setting, a focal spot selection, source-to-image distance, source-to-patient distance, and orthogonality. Also, user-input commands 160 include movement of the X-ray source 16. This movement may include the movement of a remotely movable X-ray source 16 to a desired position via either the movement of the overhead tube support arm 14 in fixed system 12 or the movement of the support arm 52 and/or support column 54 in a mobile system 12. The user-input commands 160 also include a movement command 164 for fine movement of the mobile system 12 via the wheeled base 58. As previously mentioned, the user-input commands 160 include a collimator light command 166 to illuminate the collimator light 66 on the region of the patient 20 that will receive X-ray radiation during an imaging sequence.

Also, patient audible commands 168 may include a signal from the device 38 to the imaging system 12 to transmit the patient-audible command 168 in response to the signal. These signals may correspond to multiple pre-recorded patient audible commands 168 stored within the control circuitry 74 of the system 12. Moreover, the patient-audible commands 168 may be pre-recorded in at least two spoken languages. The patient-audible commands 168 may be transmitted via the system speaker 44. A user, then, who does not speak a particular language may nevertheless issue instructions to the patient in the patient's language simply by selecting the desired instructional message via the handheld device. Also, as mentioned above, certain embodiments of the handheld interface device 38 (e.g., 42) may be configured to receive, to record, and/or transmit user-dictated voice inputs 170. The transmitted user-dictated voice inputs 170 may be received by the imaging system 12 and emitted for the patient 20 undergoing X-ray imaging to hear.

Figure 10:
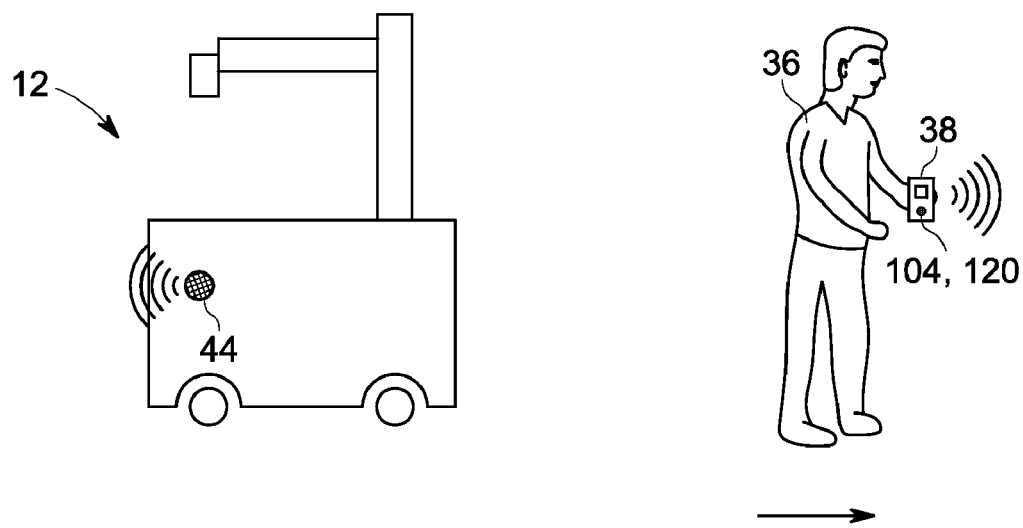
FIG. 10 is a perspective view of an imaging system and handheld interface device outside of a desired distance from each other, in accordance with aspects of the present technique.

FIGS. 10-17 that follow illustrate various scenarios for the use of the handheld interface device 38 and/or interaction with the imaging system 12. FIG. 10 illustrates a scenario where the handheld interface device 38 and the imaging system 12 are outside a desired range. The imaging system 12 illustrated is mobile, but the system 12 may also be fixed. The imaging system 12 and/or the handheld interface device 38 are configured to determine the strength of the wireless signals between each other. A preset desired wireless strength that corresponds to a specific distance between the device 38 and the system 12 may be set. This preset desired wireless strength may vary depending upon the setup of the X-ray system 10. As the user 36 moves away from the system 12 with the device 38 the wireless strength decreases. If the wireless strength falls below the preset desired wireless strength, then the imaging system 12 and/or the handheld interface device 38 are configured to emit a user-perceptible signal (e.g., audible tone via speakers 44, 104, and/or 120) to indicate that the system 12 and the device 38 are greater than a desired distance apart.

Figure 11:
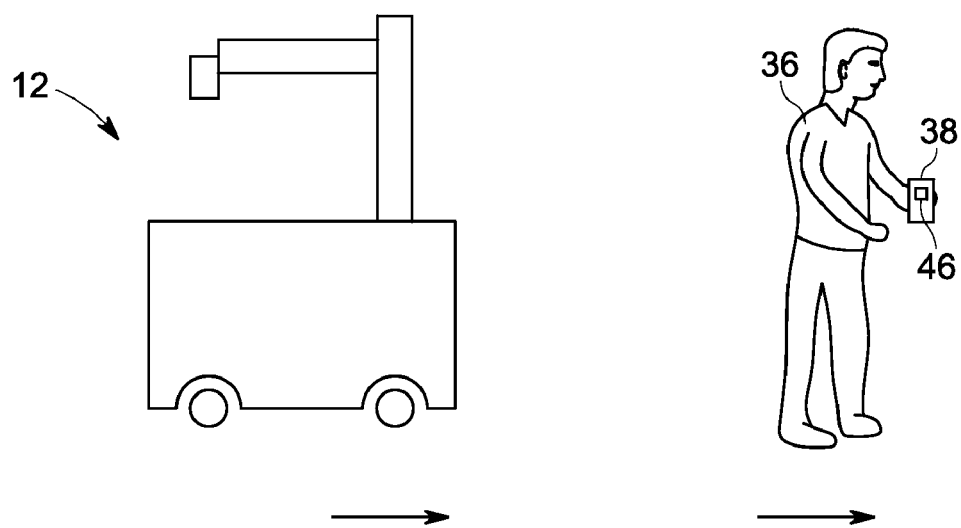
FIG. 11 is a perspective view of the imaging system following the handheld interface device, in accordance with aspects of the present technique.

As mentioned above, certain embodiments of the handheld interface device 38 (e.g., 42) may include tracking devices 144 or the device may be configured to perform tracking based on signal strength, or a similar parameter. FIG. 11 illustrates a scenario where the tracking device 144 allows the imaging system 12 to follow the handheld interface device 38. The imaging system 12 illustrated is a mobile system. The imaging system 12 is configured to track the location and/or movement of the handheld interface device via the tracking device 144 located within device 38. The user 36 may input a command via one of the input devices available on the handheld interface device 38 (e.g., screen 46) for the system 12 to follow the device 38. As the user 36 moves throughout a building, the system 12 tracks the location of the handheld interface device 38 via the tracking device 144 and follows the device 38 as it is displaced. This may dispense with the need for the system to be guided, pushed or driven for at least some of its movement through an institution.

Figure 12:
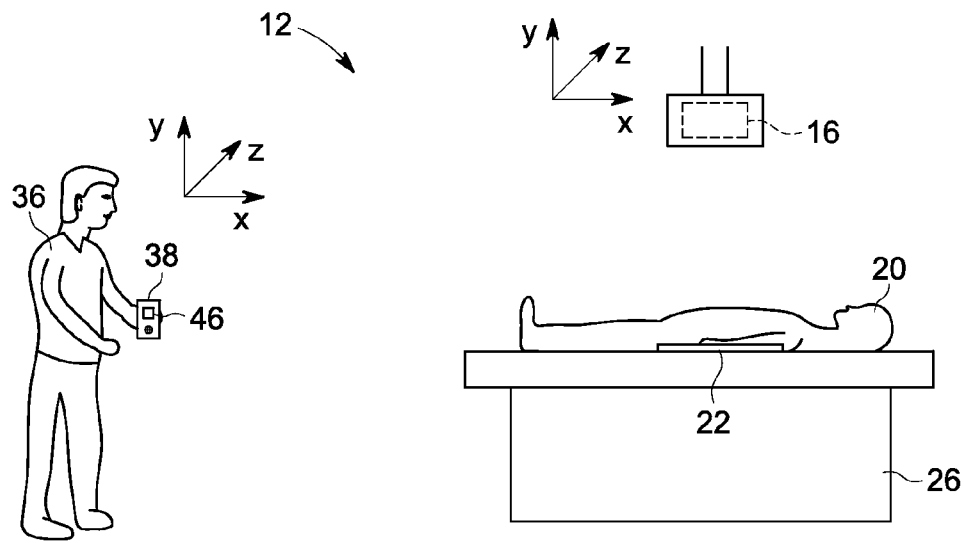
FIG. 12 is a perspective view of movement of an X-ray source of the imaging system by the handheld interface device, in accordance with aspects of the present technique.

Another use for the tracking device 144 of the handheld interface device 38 is shown in FIG. 12. FIG. 12 illustrates the imaging system 12 with the patient 20 located on the table 26 between the X-ray source 16 and the image receptor 22. The imaging system 12 may be a fixed or mobile system. The X-ray source 16 may be moved to a desired position via either the movement of the overhead tube support arm 14 in the fixed system 12 or the movement of the support arm 52 and/or support column 54 in the mobile system 12. As above, the user may input a command via one of the input devices available on the handheld interface device 38 (e.g., screen 46) for the system 12 to move the X-ray source 16 based upon the location and/or movement of the handheld interface device 38 to the desired position. As the handheld interface device 38 is moved within a 3-D coordinate system along an x, y, and z axes, the X-ray source 16 is correspondingly moved along the same axes to the desired position.

Figure 13:
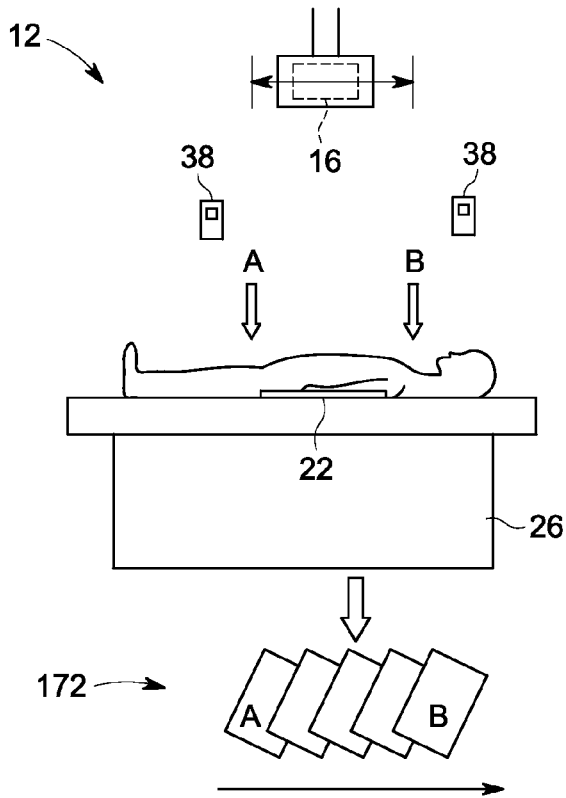
FIG. 13 is a perspective view of the imaging system conducting an imaging sequence in response to the handheld interface device, in accordance with aspects of the present technique.

The tracking device 144 can also similarly be used to provide an input to the imaging system 12 to perform a desired X-ray image data acquisition sequence. FIG. 13 illustrates the use of the handheld interface device 38 to perform a desired imaging sequence. The illustrated imaging system 12 is as described in FIG. 12. The user 36 may select an image acquisition sequence mode via one of the input devices available on the handheld interface device 38 (e.g., screen 46). Once in the acquisition mode, the imaging system 12 is configured to record one or more locations of the handheld interface device 38 via the tracking device 144 and to use the recorded locations as input for an X-ray imaging sequence. The recorded locations may be used as inputs for determining a tomographic sweep by the X-ray source 16. For example, using the input devices on the handheld interface device 38, a first location, A, may be selected and then recorded by the system 12. Then, similarly the device 38 may be used to select a second location, B, to be recorded by the system 12. Upon initiation of the X-ray imaging sequence, the radiation source 16 moves between locations A and B performing the desired imaging sequence (e.g., tomographic sweep) generating multiple images 172 between those locations.

FIG. 14 illustrates the use of the handheld interface device 38 to compute various exposure parameters. The imaging system 12 illustrated is as described in FIG. 12. The handheld interface device 38 and the tracking device 144 may be used to input the location of the device 38 as described above. The imaging system 12 is configured to use the location of the device 38 for the computation of various exposure parameters, such as source-to-image distance (SID) 174, source-to-patient distance 176, and patient thickness 178. The SID 176 is determined by placing the handheld interface device 38 at the image receptor 22 and inputting the location of the device 38 (location A). The system 12 uses location A with respect to the X-ray source 16 in the computation of SID 176. The source-to-patient distance 176 is similarly determined by placing the handheld interface device 38 on the patient 20 where the exposure is to take place and inputting the location of the device 38 (location B). The imaging system 12 then takes the difference between the source-to patient distance 176 and the SID 174 for the computation of the patient thickness 178. The patient thickness 178 may be used by the imaging system 12 to set an X-ray dose parameter for the exposure.

FIG. 15 illustrates a further use of the handheld interface device 38. The imaging system 12 is illustrated with the patient 20 located on an inclined surface 180 (e.g., bed 60) between the X-ray source 16 and the image receptor 22. The image receptor 22 may have a grid 182 located on the image receptor 22 to reduce the scattering of the X-rays. The imaging system 12 may be a fixed or mobile system. The X-ray source 16 may be moved to a desired position via either the movement of the overhead tube support arm 14 in the fixed system 12 or the movement of the support arm 52 and/or support column 54 in a mobile system 12. As above, the user places the handheld interface device 38 on the image receptor 22 and/or grid 182 and inputs a command via one of the input devices to transmit the location of the device 38 as derived from the tracking device 144 and thus the relative location of the image receptor 22 and/or grid 182 to the system 12. The inputted location of the handheld interface device 38 is used to compute the orthogonality between the image receptor 22 and/or grid 182 with respect to the X-ray source 16. The calculated orthonogonality is displayed on the screen 46 of the handheld interface device 38. Based on the calculated orthogonality the imaging system 12 also may move the X-ray source 16 along a desired x, y, and z axes. For example, the X-ray source may be initially positioned in a first position, A. After determining the orthogonality between the X-ray source 16 and image receptor 22 and/or grid 182, the system 12 may move the X-ray source 16 to a second position, B, with the desired orthogonality.

Figure 16:
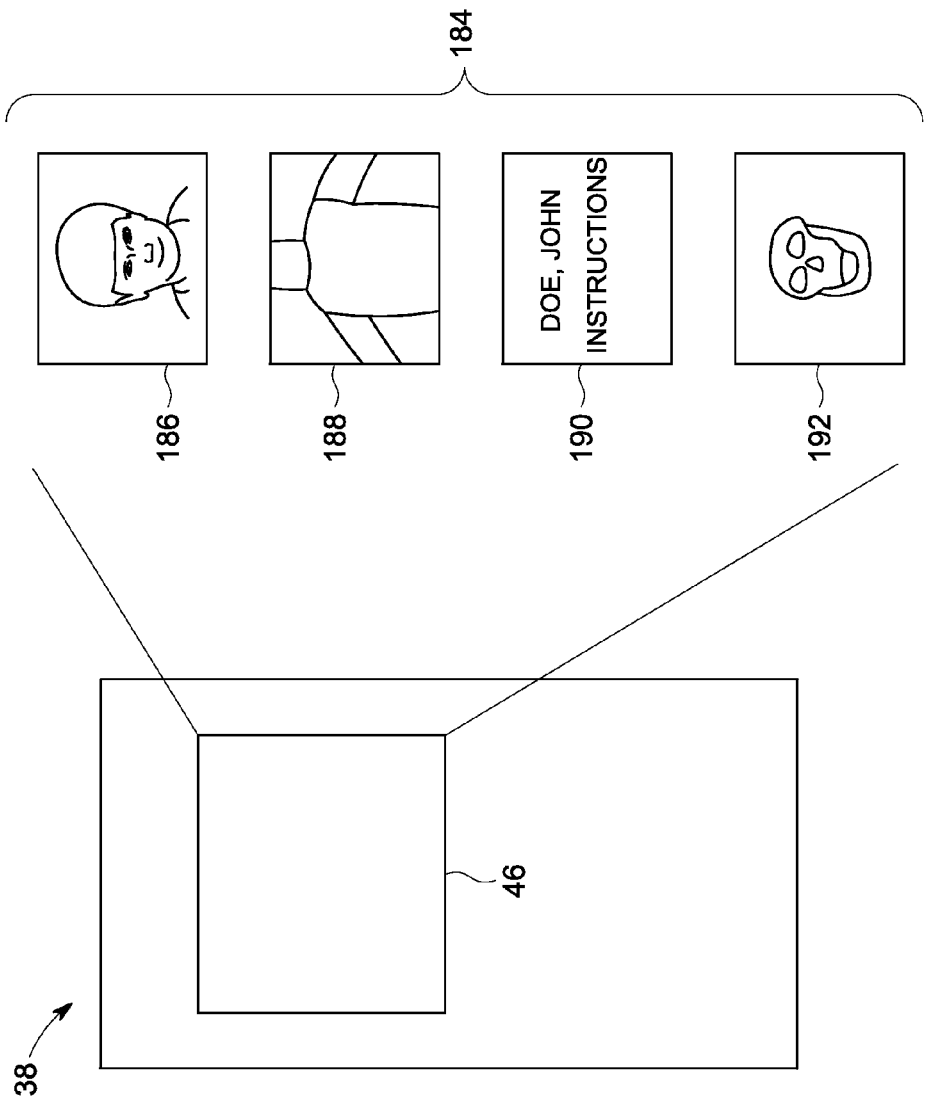
FIG. 16 is perspective view of various patient data displayed on the handheld interface device, in accordance with aspects of the present technique.

The handheld interface device 38 has additional features. In embodiments of the handheld interface device 38 with a screen 46 (e.g., 42), the screen 46 is configured to display patient data 184 as illustrated in FIG. 16. Types of patient data 184 include an identifying image 186 of the patient 20. The identifying image 186 may be provided via the network 48 or the imaging system 12. The system 12 may also provide an image 188 of the patient 20 or a portion of the anatomy of the patient 20 to receive X-ray radiation via the system camera 24. The image 188 may be a still or live image. Also, the image 188 may be a generic image representative of an anatomical region of the patient 20. Additional patient data 184 displayed by the screen includes patient identifying data 190 such as the name of the patient, the anatomy to be imaged, the types of images, and further instructions or information. The screen 46 also displays reconstructed X-ray images 192 of the patient 20 received from the system 12 (in digital X-ray systems 10).

Figure 17:
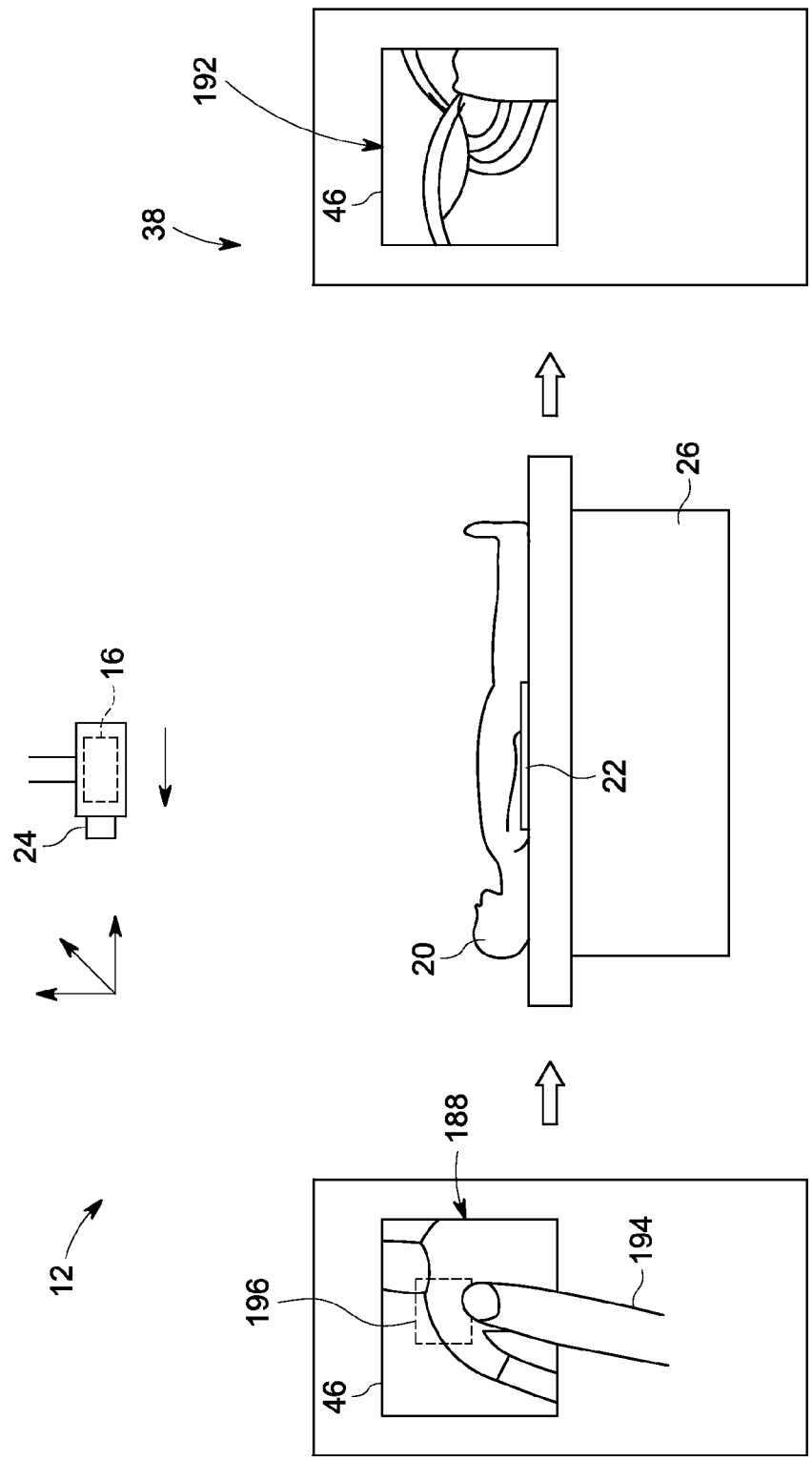
FIG. 17 is a perspective view of selection of desired area for imaging using the handheld interface device, in accordance with aspects of the present technique.

FIG. 17 illustrates the use of the screen 46 to control the movement of the X-ray source 16. The illustrated imaging system 12 is as described above. The user receives the image 188 of the patient 20 on the screen 46 of the handheld interface device 46. The screen 46 illustrated is touch-screen 46 capable of encoding inputs by the touch of the user. The user uses a finger or other object 194 to input a selection 196 of a specific part of the patient anatomy for exposure. The device 38 transmits a signal to the imaging system 12 specifying the desired anatomy for exposure to X-ray radiation. The imaging system 12 is configured to move the X-ray source 16 into position to take the desired exposure. Then, the system 12 (in a digital X-ray system 10) is configured to process X-ray image data and to generate the reconstructed image 192 of the desired anatomy. The screen 46 of the handheld interface device 38 displays the reconstructed image 192 of the desired anatomy.

Figure 18:
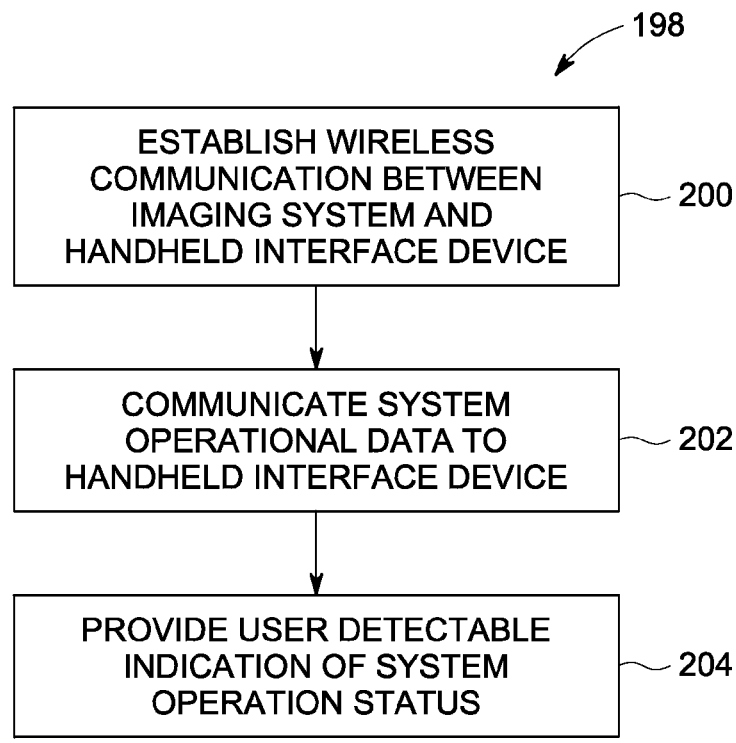
FIG. 18 is a flow diagram of a method for operating the handheld interface device, in accordance with aspects of the present technique.

FIGS. 18-21 illustrate various methods for operation of the handheld interface device 38. FIG. 18 illustrates a flow diagram of a method 198 for operating the handheld interface device 38. The method 198 includes establishing wireless communication between the imaging system 12 and the handheld interface device 38 (block 200). The system 12 includes the components described above in FIG. 3. The imaging system 12 and the handheld interface device 38 communicate via their respective wireless interfaces 76 and 124. Following the establishment of a wireless link, system 12 communicates system operational data 146 to the handheld interface device 38 (block 202). The handheld interface device 38 then provides a user detectable indication of the operational status of the imaging system 12 based upon the received data 146 (block 204). The user detectable indication includes vibration of the device 38, illumination from LEDS, among other indications.

Figure 19:
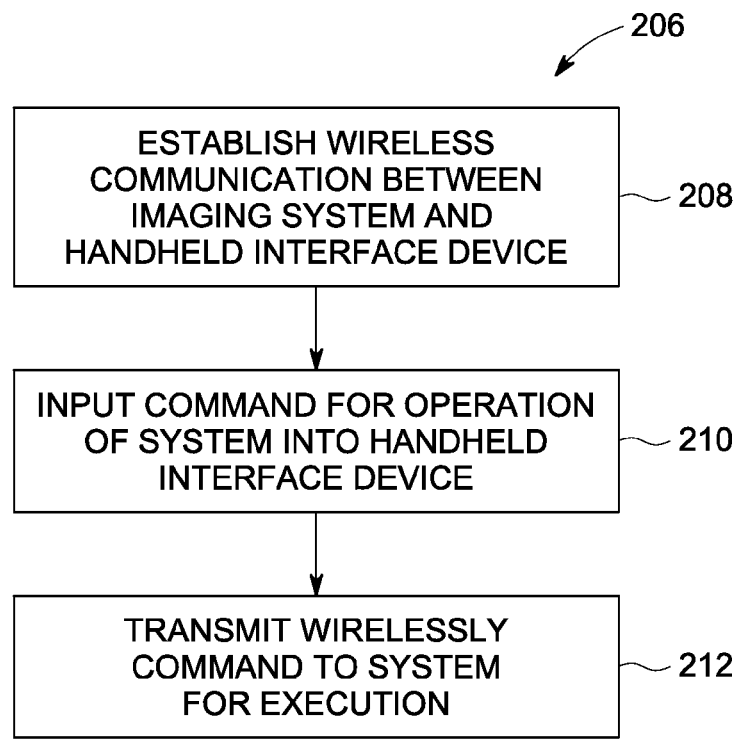
FIG. 19 is a flow diagram of another method for operating the handheld interface device, in accordance with aspects of the present technique.

FIG. 19 illustrates another flow diagram of a method 206 for operating the handheld interface device 38. The method 206 includes establishing wireless communication between the system 12 and device 38 (block 208) as described in method 198. After establishing a wireless link, the user inputs a command into the handheld interface device 38 for operation of the imaging system 12 (block 210). The user-input command 160 may include the movement of the X-ray source 16 or the fine movement of the system 12, if mobile, as an example. Following input of the command, the handheld interface device 38 wirelessly transmits the command to the system (block 212), whereupon the imaging system 12 is configured to receive and execute the command for operation of the system 12.

Figure 20:
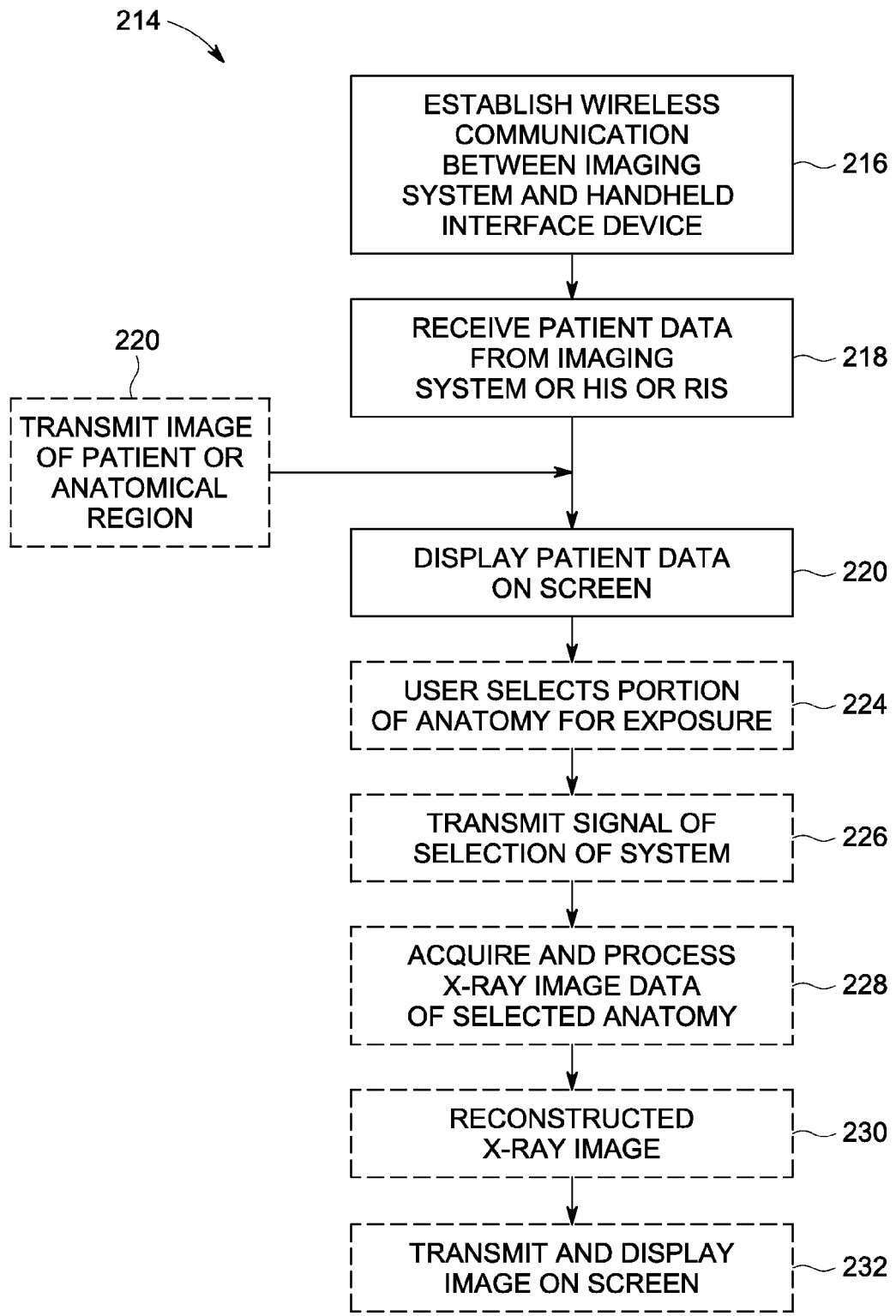
FIG. 20 is a flow diagram of a method for viewing patient data on the handheld interface device, in accordance with aspects of the present technique.

FIG. 20 illustrates a flow diagram of a method 214 for viewing patient data on a handheld interface device 38. The method 214 includes establishing wireless communication between the system 12 and device 38 (block 216) as described in method 198. The handheld interface device 38 includes user-viewable screen 46 configured to display patient data 184 and to receive a user input (e.g., touch-screen 46). After establishing a wireless link, the handheld interface device receives patient data 184 either from the imaging system 12 or the HIS 88 or RIS 86 of the medical facility's network 48 (block 218). The imaging 12 may also transmit the image 188 of the patient 20 or anatomical region of the patient 20 to the device 38 (block 220) via the system camera 24. Alternatively, the image 188 (e.g., generic image representative of anatomical region of patient 20) may be provided by the network 48. After receiving the patient data 184, the data 184 is displayed on the screen 46 (block 222). If the patient data consists of the image 188 of the patient 20, the user may select a desired portion of the anatomy for exposure (block 224). The selection 196 may be transmitted as a signal to the system 12 (block 226) for that region to be imaged. In response to the signal, the X-ray source 16 may need to be moved to make the desired exposure. The system 12 (in a digital X-ray system 10) may then acquire and process X-ray image data of the selected anatomy (block 228). Then, the system 12 may generate a reconstructed X-ray image 192 (block 230). This reconstructed X-ray image 192 may be transmitted to and displayed on the screen 46 of the handheld interface device 38 (block 232).

Figure 21:
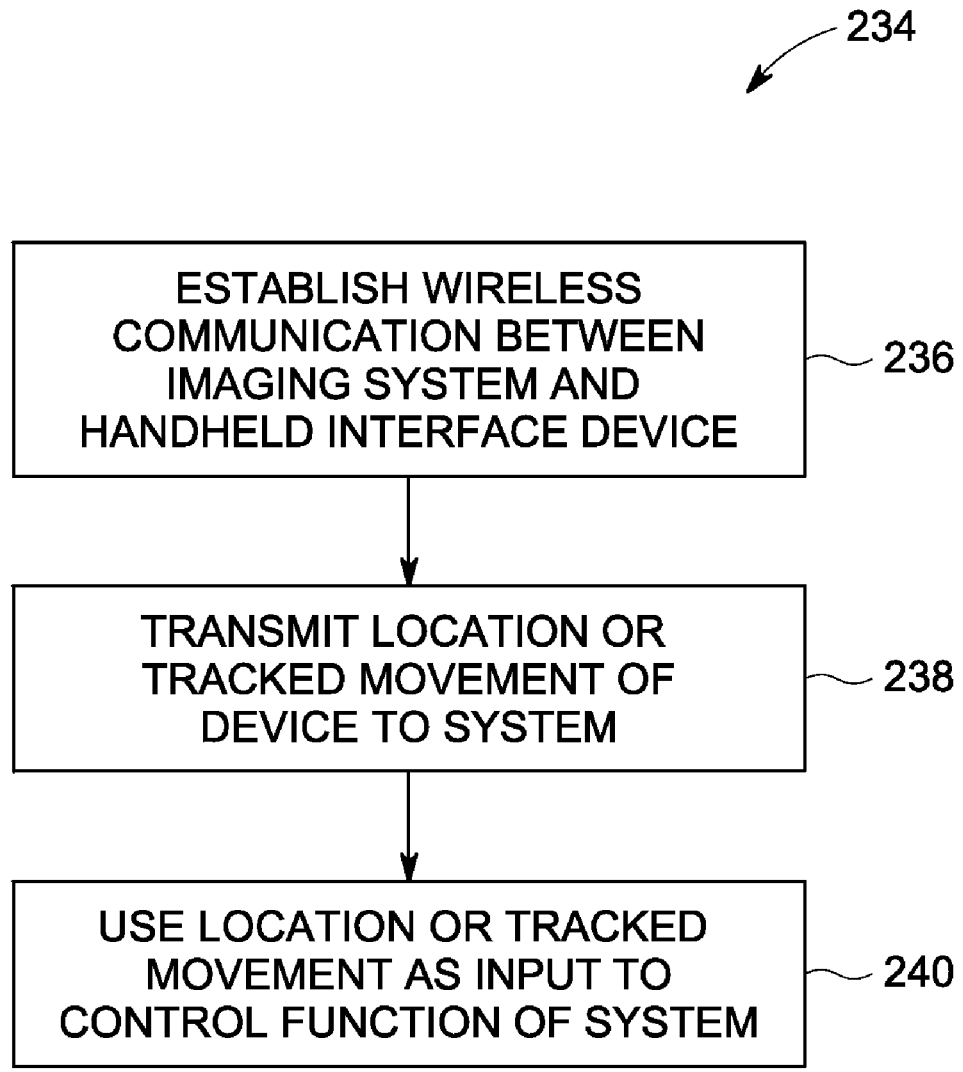
FIG. 21 is a flow diagram of a method for tracking the location of the handheld interface device, in accordance with aspects of the present technique.

FIG. 21 illustrates a flow diagram of a method 234 for tracking the location of the handheld interface device 38. The method 234 includes establishing wireless communication between the system 12 and device 38 (block 236) as described in method 198. The handheld interface device 38 includes tracking device 144 which is configured to provide a location and to track movement of the handheld interface device. After establishing a wireless link, the tracked location and/or movement of the handheld interface device 38 is transmitted to the imaging system 12 (block 238). The imaging system 12 then uses the tracked location and/or position as input to control at least one function of the system 12 (block 240). For example, the input may be used to direct the system 12, if mobile, to follow the handheld interface device 38.

The handheld interface device 38 described above provides the user increased information about the imaging system 12 while allowing the user to work at a distance from the system 12 and providing a safer environment. The wireless design alleviates the problems typically associated with a cord, such as interference with medical equipment or damage to the cord over time. Additionally, the user may find the device 38 if ever lost via a locator signal. Further, the device 38 provides the user three different types of feedback mechanisms to indicate a current exposure including visual, audible, and tactile (vibrations).

The more advanced features of the handheld interface device 38 provide the user more flexibility in controlling the system 12, particularly in light of advanced user control features provided by the touch-screen 46 and the tracking device 144. For example, the advanced features would assist in allowing the user to better position the system 12 and image receptor 22, particularly when the patient 20 is in a complicated position, for acquiring an improved image.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. An X-ray system comprising:
an imaging system including a source of X-ray radiation, an X-ray image receptor, control circuitry for controlling the source of X-ray radiation, and a wireless interface; and
a handheld interface device configured to communicate wirelessly with the imaging system;
wherein the imaging system is configured to track a location of the handheld interface device and to use the location as an input for at least one control function of the imaging system, and the imaging system is configured to record at least one location of the handheld interface device and to use the recorded location as input for an X-ray image acquisition sequence.

2. The system of claim 1, wherein the imaging system is mobile, and is configured to follow the handheld interface device as it is displaced in a building.

3. The system of claim 1, wherein the imaging system is configured to command movement of the X-ray source based upon the location of the handheld interface device.

4. The system of claim 1, wherein the imaging system is configured to record a plurality of locations of the handheld interface device and to use the recorded locations as inputs for determining a tomographic sweep by the X-ray source.

5. The system of claim 1, wherein the imaging system is configured to use the location of the handheld interface device for computation of a source-to-image distance.

6. The system of claim 5, wherein the imaging system is configured to use a further location of the handheld interface device for computation of a source-to-patient distance.

7. The system of claim 6, wherein the imaging system is configured to use the source-to-image distance and the source-to-patient distance for computation of a patient thickness.

8. The system of claim 7, wherein the imaging system is configured to use the computed patient thickness to set an X-ray dose parameter.

9. The system of claim 1, wherein the imaging system is configured to use the location of the handheld interface device for computation of orthogonality between the image receptor and the X-ray source.

10. An X-ray system comprising:
a handheld X-ray interface device comprising a wireless interface for communicating with an imaging system, a tracking device configured to provide a location and/or to track movement of the handheld X-ray interface device relative to the imaging system, and an input device configured to indicate to the imaging system to record the location of the handheld X-ray interface device, wherein the location or tracked movement of the handheld X-ray interface device is communicated to the imaging system as an input for at least one control function of the imaging system, and the handheld X-ray interface device is configured to command the imaging system to perform a specific X-ray image acquisition sequence by using a recorded location of the handheld X-ray interface device as input.

11. The system of claim 10, wherein the tracking device comprises an accelerometer, a magnetometer, an inclinometer, or a gyroscope.

12. The system of claim 10, wherein the handheld X-ray interface device is configured to command movement of the imaging system via the location or tracked movement of the handheld X-ray interface device.

13. The system of claim 10, wherein the handheld X-ray interface device is configured to provide the location of the handheld X-ray interface device to the imaging system for computation of a source-to-image distance.

14. The system of claim 13, wherein the handheld X-ray interface device is configured to provide a further location of the handheld X-ray interface device to the imaging system for computation of a source-to-patient distance.

15. A method for tracking the location of a handheld interface device, comprising:
establishing wireless communication between an imaging system and a handheld interface device, the imaging system comprising a source of X-ray radiation, an X-ray image receptor, control circuitry for controlling the source of X-ray radiation, and a first wireless interface, the handheld interface device comprising a second wireless interface for communicating wirelessly with the imaging system and a tracking device configured to provide a location and to track movement of the handheld interface device;
transmitting the location or tracked movement of the handheld interface device relative to the imaging system;
using the location or tracked movement of the handheld interface device as an input to control at least one function of the imaging system;
the imaging system recording the location or tracked movement of the handheld interface device transmitted from the handheld interface device; and
the imaging system utilizing the recorded location or tracked movement of the handheld interface device as input for an X-ray image acquisition sequence.

16. The method of claim 15, wherein the imaging system is mobile, and is configured to follow the handheld interface device as it is displaced in a building.

* * * * *